US012697038B2

(12) United States Patent
Brooks et al.

(10) Patent No.: US 12,697,038 B2
(45) Date of Patent: Aug. 4, 2026

(54) ACTIVITY MONITORING TO AUGMENT PERSONALIZED BLOOD PRESSURE MODEL

(71) Applicant: QUALCOMM Incorporated, San Diego, CA (US)

(72) Inventors: Emily Kathryn Brooks, Amherst, NY (US); John Keith Schneider, Williamsville, NY (US); Vivekananda Parampalli Adiga, Williamsville, NY (US); Shounak Uday Gore, Hyderabad (IN); Nicholas Buchan, San Jose, CA (US); Hrishikesh Vijaykumar Panchawagh, Cupertino, CA (US); Evan Michael Breloff, Kenmore, NY (US); Ye Zhan, Buffalo, NY (US)

(73) Assignee: QUALCOMM Incorporated, San Diego, CA (US)

( * ) Notice: Subject to any disclaimer, the term of this patent is extended or adjusted under 35 U.S.C. 154(b) by 144 days.

(21) Appl. No.: 18/486,866

(22) Filed: Oct. 13, 2023

(65) Prior Publication Data

US 2025/0120598 A1     Apr. 17, 2025

(51) Int. Cl.
    A61B 5/021        (2006.01)
    A61B 5/00         (2006.01)
(52) U.S. Cl.
    CPC ........ A61B 5/02125 (2013.01); A61B 5/0095 (2013.01); A61B 5/681 (2013.01)
(58) Field of Classification Search
    CPC .... A61B 5/02125; A61B 5/0095; A61B 5/681
    See application file for complete search history.

(56) References Cited

U.S. PATENT DOCUMENTS

| | | | |
|---|---|---|---|
| 2013/0109947 A1 | 5/2013 | Wood | |
| 2015/0065826 A1* | 3/2015 | Mulligan | A61B 5/7246 600/323 |
| 2019/0082984 A1* | 3/2019 | Han | A61B 5/7221 |
| 2020/0397312 A1 | 12/2020 | Ben Oren et al. | |
| 2022/0175258 A1 | 6/2022 | Kitchens et al. | |

OTHER PUBLICATIONS

"Glabella: Continuously Sensing Blood Pressure Behavior using an Unobtrusive Wearable Device" by C. Holz et al. Proc. ACM Interact Mob Wear Ubiq Tech. vol. 1, Issue 3. Article No. 58, pp. 1-23, Sep. 2017.*

International Search Report and Written Opinion—PCT/US2024/046311—ISA/EPO—Jan. 13, 2025.

* cited by examiner

*Primary Examiner* — Jason M Ip
(74) *Attorney, Agent, or Firm* — Weaver Austin Villeneuve & Sampson LLP

(57)                 ABSTRACT

In some implementations, an apparatus may obtain activity information indicative of an activity performed by a person. The apparatus may update a model for determining blood pressure of the person based at least in part on the obtained activity information. The apparatus may detect an acoustic wave corresponding to a photoacoustic response of a blood vessel of the person to light emitted by a light source system. The apparatus may estimate a blood pressure based at least in part on the updated model and the acoustic wave. In some embodiments, the apparatus may comprise a wearable device worn by the person.

24 Claims, 12 Drawing Sheets

400

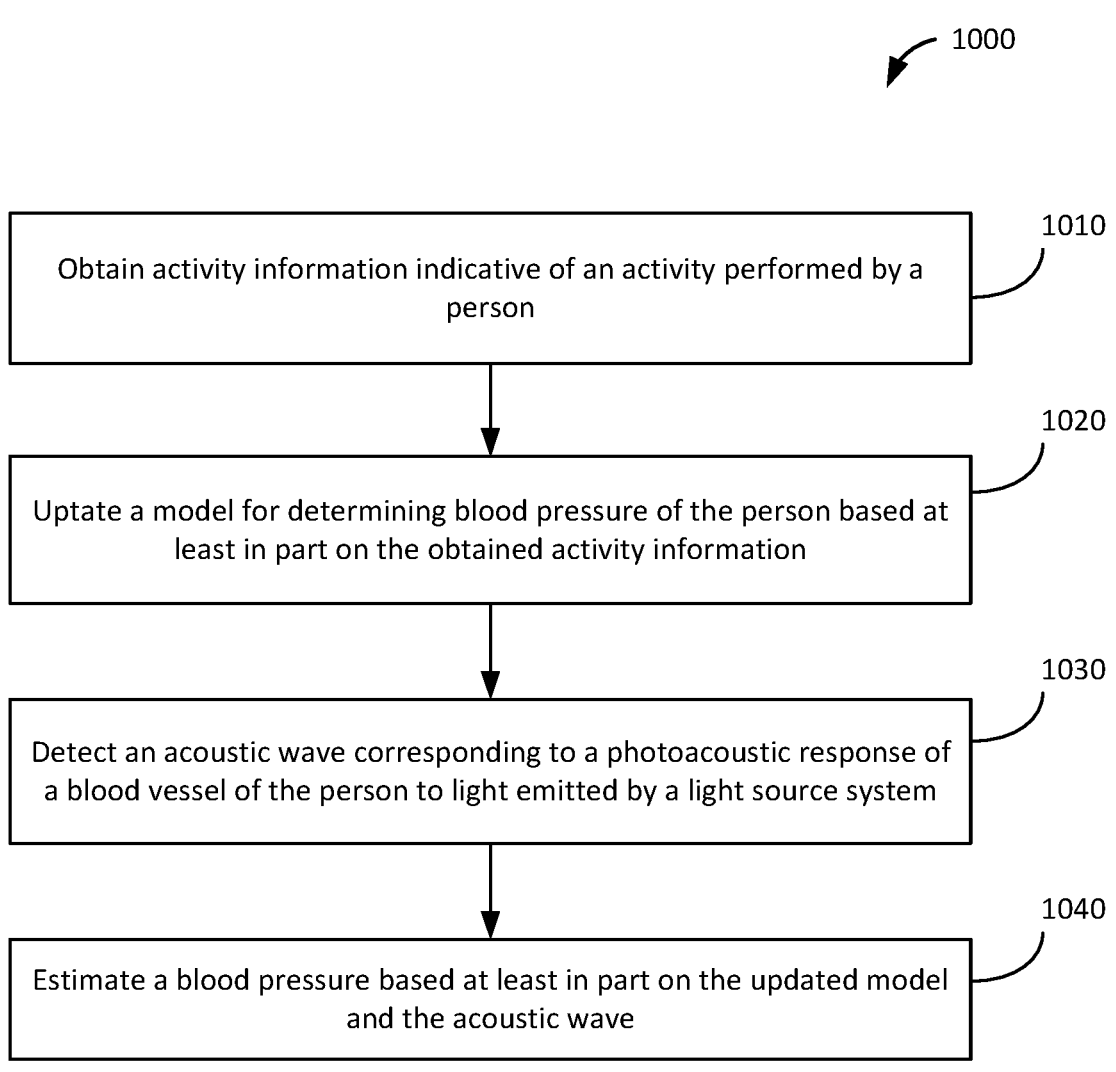

1000

Obtain activity information indicative of an activity performed by a person

1010

Uptate a model for determining blood pressure of the person based at least in part on the obtained activity information

1020

Detect an acoustic wave corresponding to a photoacoustic response of a blood vessel of the person to light emitted by a light source system

1030

Estimate a blood pressure based at least in part on the updated model and the acoustic wave

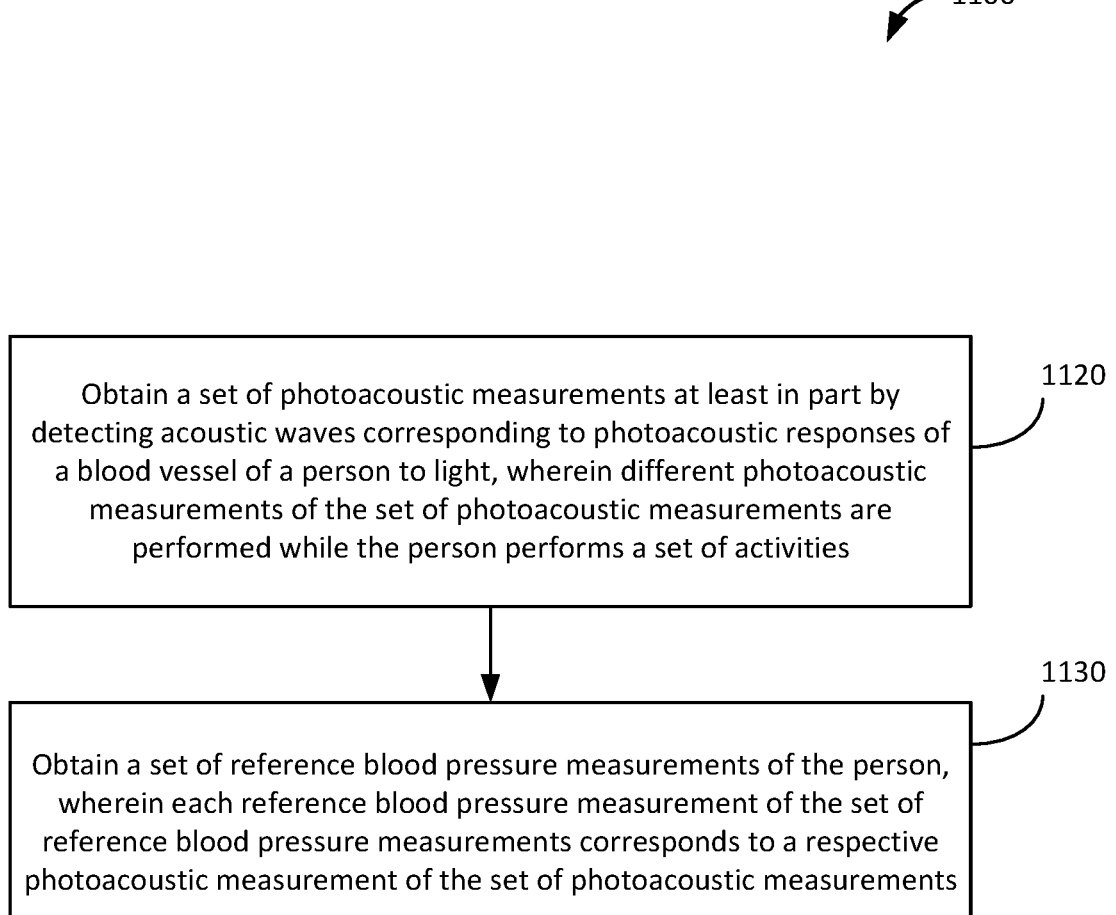

1100

1120

Obtain a set of photoacoustic measurements at least in part by detecting acoustic waves corresponding to photoacoustic responses of a blood vessel of a person to light, wherein different photoacoustic measurements of the set of photoacoustic measurements are performed while the person performs a set of activities

1130

Obtain a set of reference blood pressure measurements of the person, wherein each reference blood pressure measurement of the set of reference blood pressure measurements corresponds to a respective photoacoustic measurement of the set of photoacoustic measurements

1140

Determine a model for estimating blood pressure of the person from subsequent photoacoustic measurements based on a correlation between the set of reference blood pressure measurements and the set of photoacoustic measurements

*Figure 11*

ACTIVITY MONITORING TO AUGMENT PERSONALIZED BLOOD PRESSURE MODEL

TECHNICAL FIELD

This disclosure relates generally to devices and systems using multiple types of sensors.

DESCRIPTION OF RELATED TECHNOLOGY

A variety of different sensing technologies and algorithms are being implemented in devices for various biometric and biomedical applications, including health and wellness monitoring. This push is partly a result of the limitations in the usability of traditional measuring devices for continuous, noninvasive and/or ambulatory monitoring. Some such devices are, or include, photoacoustic sensors or optical sensors. Although some previously deployed devices can provide acceptable results, improved detection devices and systems would be desirable.

SUMMARY

The systems, methods, and devices of this disclosure each have several aspects, no single one of which is solely responsible for the desirable attributes disclosed herein.

An example apparatus comprising: a control system configured to obtain activity information indicative of an activity performed by an apparatus user, and update a model for determining blood pressure of the apparatus user based at least in part on the obtained activity information. The one or more processors further may be configured to a light source system including a light-emitting component, a receiver system configured to detect an acoustic wave corresponding to a photoacoustic response of a blood vessel of the apparatus user to light emitted by the light source system, wherein the control system is further configured to estimate a blood pressure based at least in part on the updated model and the acoustic wave.

An example method of blood pressure estimation, according to this disclosure, may comprise obtaining activity information indicative of an activity performed by a person. The method also may comprise updating a model for determining blood pressure of the person based at least in part on the obtained activity information. The method also may comprise detecting an acoustic wave corresponding to a photoacoustic response of a blood vessel of the person to light emitted by a light source system. The method also may comprise estimating a blood pressure based at least in part on the updated model and the acoustic wave.

An example apparatus comprising: means for obtaining activity information indicative of an activity performed by a person. The apparatus further may comprise means for updating a model for determining blood pressure of the person based at least in part on the obtained activity information. The apparatus further may comprise means for detecting an acoustic wave corresponding to a photoacoustic response of a blood vessel of the person to light emitted by a light source system. The apparatus further may comprise means for estimating a blood pressure based at least in part on the updated model and the acoustic wave.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 10 is a flow diagram of a method of augmenting a personalized blood pressure model using activity monitoring, according to an embodiment.

FIG. 11 is a flow diagram of another method 1100 of augmenting a personalized blood pressure model using activity monitoring, according to an embodiment.

Like reference numbers and designations in the various drawings indicate like elements.

DETAILED DESCRIPTION

Figure 1:
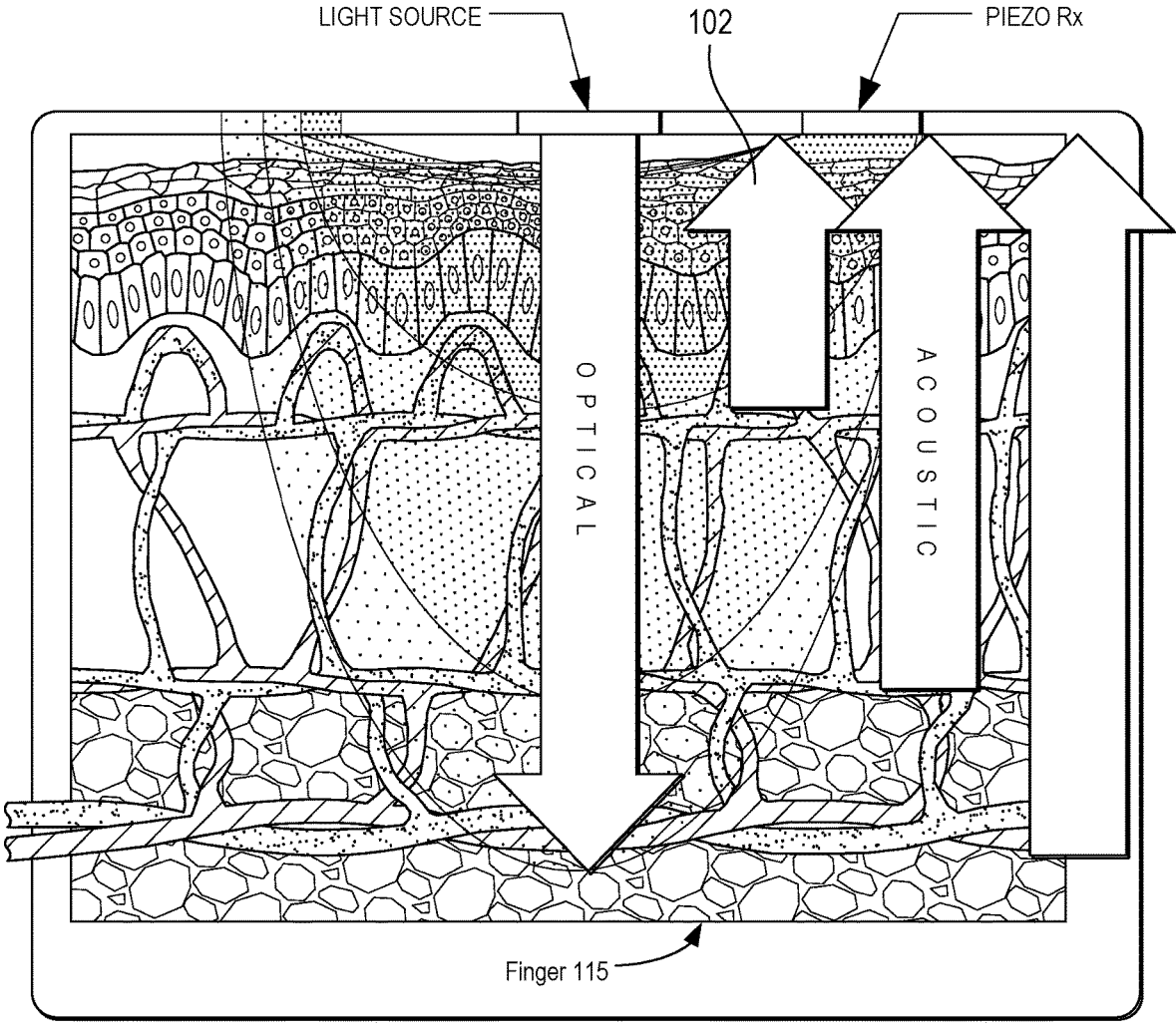
FIG. 1 shows an example of a blood pressure monitoring device based on photoacoustic plethysmography, which may be referred to herein as PAPG.

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications or monitoring of other physiological parameters. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, chest bands, anklets, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, DVD players, CD players, VCRs, radios, portable memory chips, washers, dryers, washer/dryers, parking meters, automobile doors, autonomous or semi-autonomous vehicles, drones, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

Accurate, non-invasive, and continuous monitoring wearable devices can be used for both clinical and consumer applications, e.g., for measuring physiological parameters such as blood pressure of a user. Measurement of arterial signals and heart rate waveforms from arteries is key to determining and predicting arterial (e.g., blood pressure) measurements. Non-invasive health monitoring devices, such as photoacoustic plethysmography (PAPG)-based devices, have various potential advantages over more invasive health monitoring devices such as cuff-based or catheter-based blood pressure measurement devices. Some wearable PAPG-based devices may include a platen or an interface for transmitting both light and acoustic signals. The platen or interface may be optically transparent and should ideally have an acoustic impedance that closely matches that of human skin. As discussed in more detail elsewhere herein, PAPG can measure various depth-discriminated artery waveforms and arterial characteristics such as diameter and pulse wave velocity, which in turn can be used to estimate blood pressure. Photoplethysmography (PPG) can also be used to monitor health of a user in a non-invasive way by transmitting light and receiving reflected light from a target object.

While PAPG and PPG alone can be useful and advantageous for non-invasive monitoring as mentioned so far, challenges still exist in obtaining accurate measurements from the target. For instance, blood pressure detection based on a single modality such as PAPG, PPG, acoustics, or pressure may not have sufficient information to result in sufficient resolution or quality of measurements of interest, especially arterial compliance and distension information. However, current, recent, and/or historical activity information may help increase the accuracy of blood pressure measurements.

Hence, various aspects provided in the present disclosure relate generally to an approach that uses activity information, indicative of an activity performed by a user, to enhance the accuracy of a blood pressure measurement of the user.

Some aspects more specifically relate to obtain activity information indicative of an activity performed by a user, update a model for determining blood pressure of the user based at least in part on the obtained activity information, detect (e.g., using a PAPG device) an acoustic wave corresponding to a photoacoustic response of a blood vessel of a user to light emitted by the light source system, and estimate a blood pressure based at least in part on the updated model and the acoustic wave. Activity information may include, for example, an identification of the activity, an indication of a category of the activity, sensor data indicative of the activity, or any combination thereof. Activity information may be sensed using, for example, a gyroscope, an accelerometer, a magnetometer, an altimeter, an inertial measurement unit (IMU), or any combination thereof. Further, in some implementations, machine learning can be used to train a machine learning model that can accurately estimate a physiological characteristic of a blood vessel (e.g., PTT, pulse wave velocity (PWV)) or parameter of a user (e.g., blood pressure), or examine such a physiological characteristic or parameter, in view of activity information.

Particular implementations of the subject matter described in this disclosure can be implemented to realize one or more of the following potential advantages. The use of activity information in the manner of the embodiments described hereafter can better determine and predict measurements that are more accurate than an individual measurement alone (e.g., PAPG or PPG) while remaining non-invasive. Additionally or alternatively, highly accurate (e.g., more invasive) measurements captured during a setup process may be used to determine an accurate model that may be subsequently used for accurate, non-invasive measurements by a wearable device. In some embodiments, the non-invasive measurements may be conducted by a wearable device, enabling the foregoing advantages in a user-friendly fashion.

Additional details will follow after an initial description of relevant systems and technologies.

FIG. 1 shows an example of a blood pressure monitoring based on photoacoustic plethysmography, which is referred to herein as PAPG. FIG. 1 shows the same examples of arteries, veins, arterioles, venules, and capillaries inside a body part, which is a finger 115 in this example. In some examples, the light source shown in FIG. 1 may be coupled to a light source system (not shown) that is disposed remotely from the body part (e.g., finger 115). In some implementations, the light source may be an opening of an optical fiber or other waveguide. Such an opening may also be connected to an opening of an interface that is contactable with the body part. In some embodiments, the light source system may include one or more LEDs, one or more laser diodes, etc. In this example, the light source has transmitted light (in some examples, green, red, infrared, and/or near-infrared (NIR) light) that has penetrated the tissues of the finger 115 in an illuminated zone.

In the example shown in FIG. 1, blood vessels (and components of the blood itself) are heated by the incident light from the light source and are emitting acoustic waves 102. In this example, the emitted acoustic waves 102 include ultrasonic waves. According to this implementation, the acoustic wave emissions 102 are being detected by an ultrasonic receiver, which is a piezoelectric receiver in this example. Photoacoustic emissions 102 from the illuminated tissues, detected by the piezoelectric receiver, may be used to detect volumetric changes in the blood of the illuminated zone of the finger 115 that correspond to physiological data within the illuminated tissues of finger 115, such as heart rate waveforms. Although some of the tissue areas shown to be illuminated are offset from those shown to be producing photoacoustic emissions 102, this is merely for illustrative convenience. It will be appreciated that the illuminated tissues will actually be those producing photoacoustic emissions. Moreover, it will be appreciated that the maximum levels of photoacoustic emissions will often be produced along the same axis as the maximum levels of illumination.

One important difference between an optical technique such as a photoplethysmography (PPG)-based system the PAPG-based method of FIG. 1 is that the acoustic waves shown in FIG. 1 travel much more slowly than the reflected light waves involved in PPG. Accordingly, depth discrimination based on the arrival times of the acoustic waves shown in FIG. 1 is possible, whereas depth discrimination based on the arrival times of the light waves in PPG may not be possible. This depth discrimination allows some disclosed implementations to isolate acoustic waves received from the different blood vessels.

According to some such examples, such depth discrimination allows artery heart rate waveforms to be distinguished from vein heart rate waveforms and other heart rate waveforms. Therefore, blood pressure estimation based on depth-discriminated PAPG methods can be substantially more accurate than blood pressure estimation based on PPG-based methods.

Figure 2:
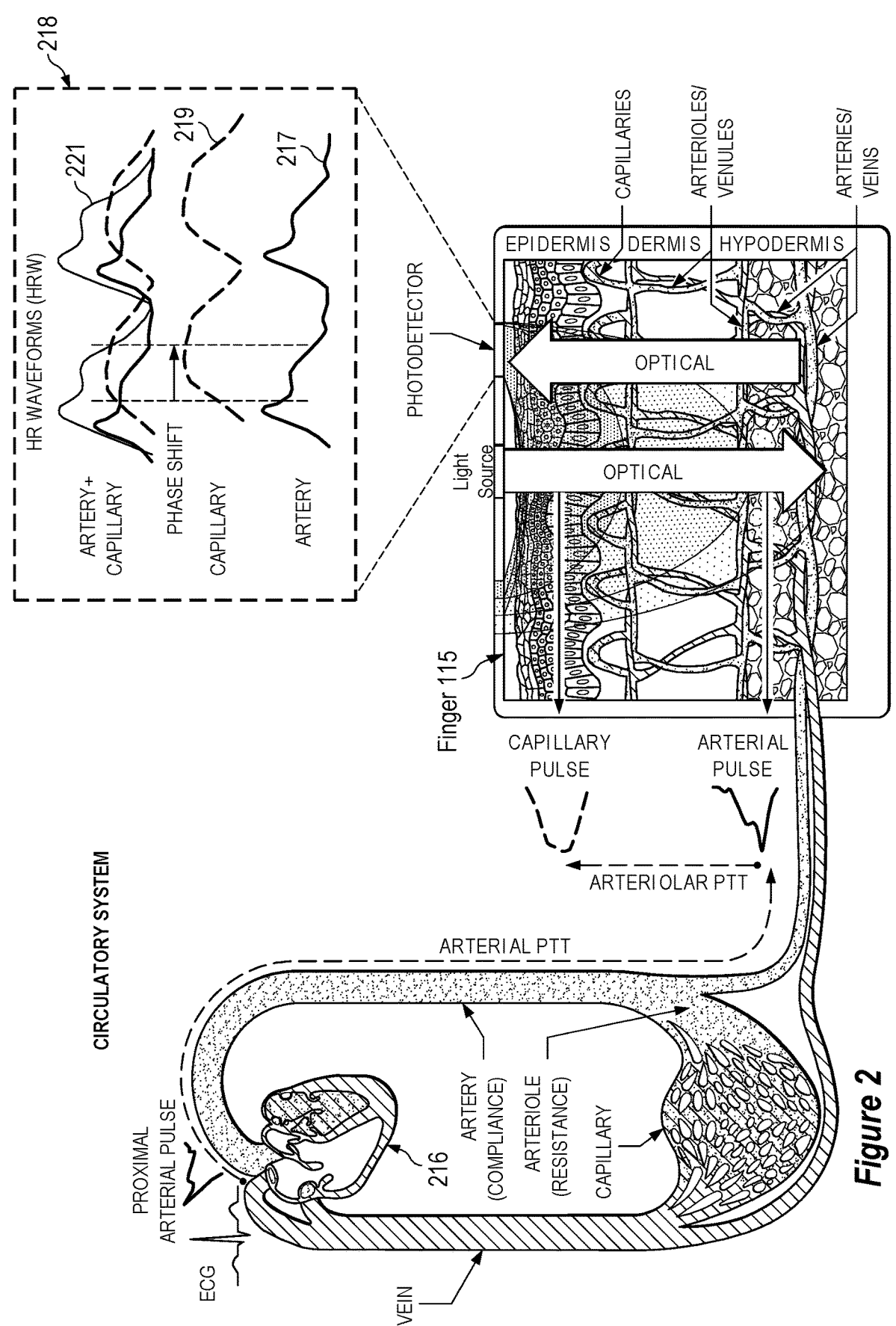
FIG. 2 shows an example of a blood pressure monitoring device based on photoplethysmography (PPG).

FIG. 2 shows an example of a blood pressure monitoring device based on photoplethysmography (PPG). FIG. 2 shows examples of arteries, veins, arterioles, venules and capillaries of a circulatory system, including those inside a finger 115. In the example shown in FIG. 2, an electrocardiogram (ECG) sensor has detected a proximal arterial pulse near the heart 216. Some examples are described below of measurement of the arterial pulse transit time (PTT) according to arterial pulses measured by two sensors, one of which may be an electrocardiogram sensor in some implementations.

According to the example shown in FIG. 2, a light source that includes one or more lasers or light-emitting diodes (LEDs) has transmitted light (in some examples, green, red, infrared, and/or near-infrared (NIR) light) that has penetrated the tissues of the finger 115 in an illuminated zone. Reflections from these tissues, detected by a photodetector, may be used to detect volumetric changes in the blood of the illuminated zone of the finger 115 that correspond to heart rate waveforms.

As shown in the heart rate waveform graphs 218 of FIG. 2, the capillary heart rate waveform 219 is differently-shaped and phase-shifted relative to the artery heart rate waveform 217. In this simple example, the detected heart rate waveform 221 is a combination of the capillary heart rate waveform 219 and the artery heart rate waveform 217. In some instances, the responses of one or more other blood vessels may also be part of the heart rate waveform 221 detected by a PPG-based blood pressure monitoring device.

Figure 3:
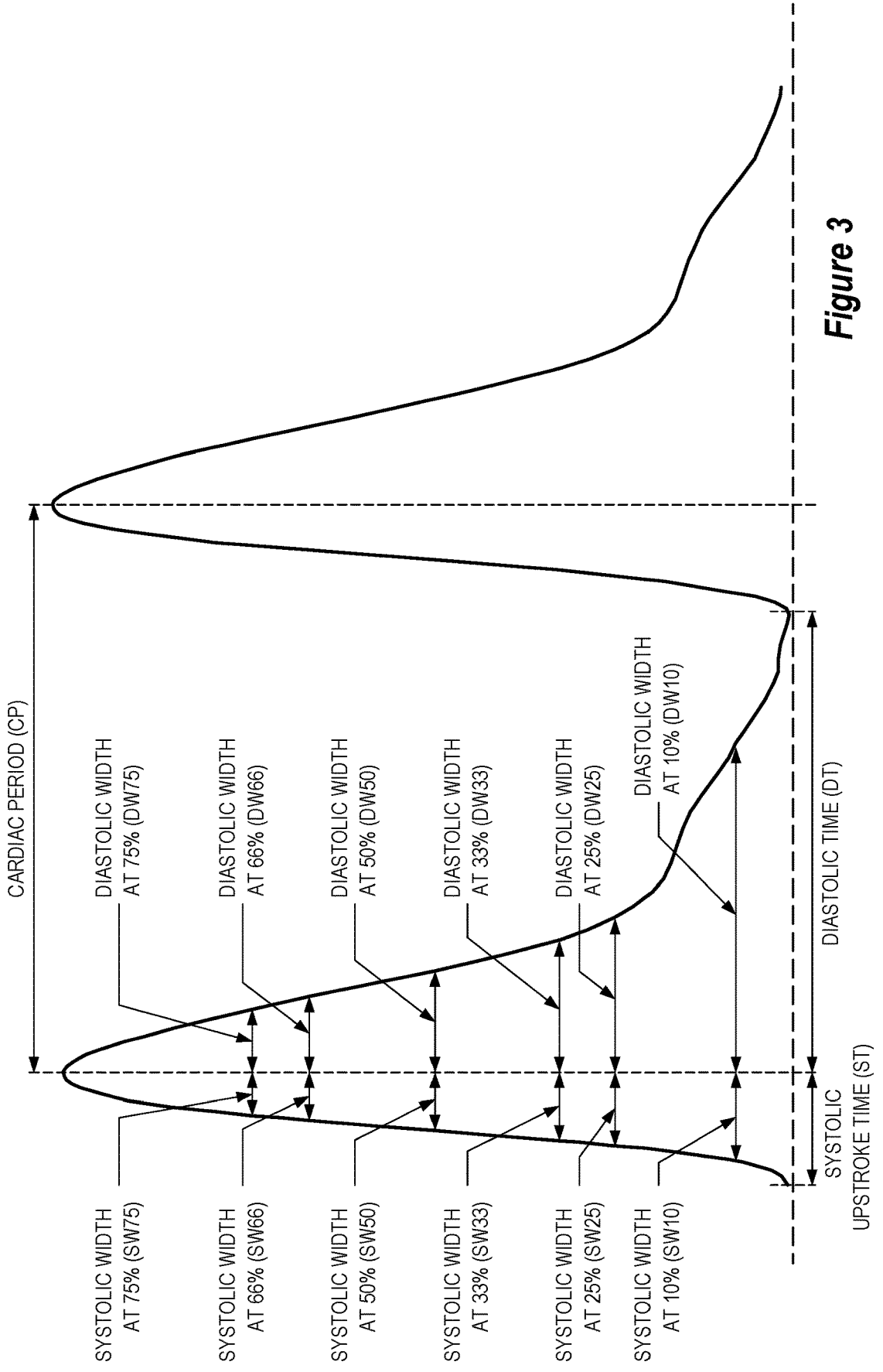
FIG. 3 shows examples of heart rate waveform (HRW) features that may be extracted according to some implementations.

FIG. 3 shows examples of heart rate waveform (HRW) features that may be extracted according to some implementations. The horizontal axis of FIG. 3 represents time and the vertical axis represents signal amplitude. The cardiac period is indicated by the time between adjacent peaks of the HRW. The systolic and diastolic time intervals are indicated below the horizontal axis. During the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

The HRW features that are illustrated in FIG. 3 pertain to the width of the systolic and/or diastolic portions of the HRW curve at various "heights," which are indicated by a percentage of the maximum amplitude. For example, the SW50 feature is the width of the systolic portion of the HRW curve at a "height" of 50% of the maximum amplitude. In some implementations, the HRW features used for blood pressure estimation may include some or all of the SW10, SW25, SW33, SW50, SW66, SW75, DW10, DW25, DW33, DW50, DW66 and DW75 HRW features. In other implementations, additional HRW features may be used for blood pressure estimation. Such additional HRW features may, in some instances, include the sum and ratio of the SW and DW at one or more "heights," e.g., (DW75+SW75), DW75/ SW75. (DW66+SW66), DW66/SW66, (DW50+SW50), DW50/SW50, (DW33+SW33), DW33/SW33, (DW25+ SW25), DW25/SW25 and/or (DW10+SW10), DW10/ SW10. Other implementations may use yet other HRW features for blood pressure estimation. Such additional HRW features may, in some instances, include sums, differences, ratios and/or other operations based on more than one "height," such as (DW75+SW75)/(DW50+SW50), (DW50+SW50)/(DW10+SW10), etc.

Figure 4:
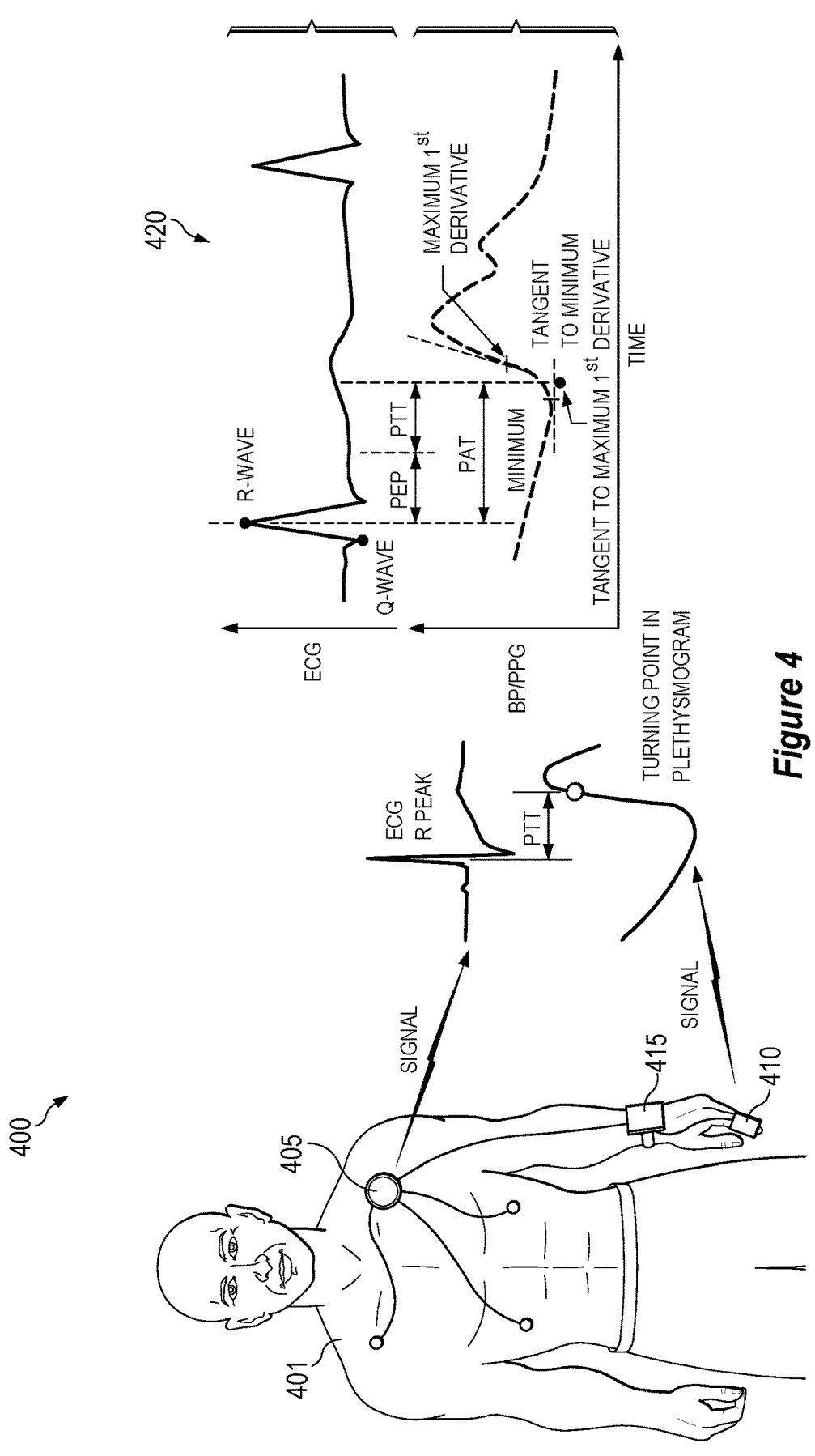
FIG. 4 shows examples of devices that may be used in a system for estimating blood pressure based, at least in part, on pulse transit time (PTT).

FIG. 4 shows examples of devices that may be used in a system for estimating blood pressure based, at least in part, on pulse transit time (PTT). As with other figures provided herein, the numbers, types and arrangements of elements are merely presented by way of example. According to this example, the system 400 includes at least two sensors. In this example, the system 400 includes at least an electrocardiogram sensor 405 and a device 410 that is configured to be mounted on a finger of the person 401. In this example, the device 410 is, or includes, an apparatus configured to perform at least some PAPG methods disclosed herein. For example, the device 410 may be, or may include, the apparatus 700 of FIG. 7 or a similar apparatus.

As noted in the graph 420, the PAT includes two components, the pre-ejection period (PEP), the time needed to convert the electrical signal into a mechanical pumping force and isovolumetric contraction to open the aortic valves) and the PTT. The starting time for the PAT can be estimated based on the QRS complex—an electrical signal characteristic of the electrical stimulation of the heart ventricles. As shown by the graph 420, in this example the beginning of a pulse arrival time (PAT) may be calculated according to an R-Wave peak measured by the electrocardiogram sensor 405 and the end of the PAT may be detected via analysis of signals provided by the device 410. In this example, the end of the PAT is assumed to correspond with an intersection between a tangent to a local minimum value detected by the device 410 and a tangent to a maximum slope/first derivative of the sensor signals after the time of the minimum value.

There are many known algorithms for blood pressure estimation based on the PTT and/or the PAT, some of which are summarized in Table 1 and described in the corresponding text on pages 5-10 of Sharma, M. et al., *Cuff-Less and Continuous Blood Pressure Monitoring: a Methodological Review* ("Sharma"), in Multidisciplinary Digital Publishing Institute (MDPI) Technologies 2017, 5, 21, both of which are hereby incorporated by reference.

Some previously-disclosed methods have involved calculating blood pressure according to one or more of the equations shown in Table 1 of Sharma, or other known equations, based on a PTT and/or PAT measured by a sensor system that includes a PPG sensor. As noted above, some disclosed PAPG-based implementations are configured to distinguish artery HRWs from other HRWs. Such implementations may provide more accurate measurements of the PTT and/or PAT, relative to those measured by a PPG sensor. Therefore, disclosed PAPG-based implementations may provide more accurate blood pressure estimations, even when the blood pressure estimations are based on previously-known formulae.

Other implementations of the system 400 may not include the electrocardiogram sensor 405. In some such implementations, the device 415, which is configured to be mounted on a wrist of the person 401, may be, or may include, an apparatus configured to perform at least some PAPG methods disclosed herein. For example, the device 415 may be, or may include, the apparatus 700 of FIG. 7 or a similar apparatus. According to some such examples, the device 415 may include a light source system and two or more ultrasonic receivers. One example is described below with reference to FIG. 6A. In some examples, the device 415 may include an array of ultrasonic receivers.

In some implementations of the system 400 that do not include the electrocardiogram sensor 405, the device 410 may include a light source system and two or more ultrasonic receivers. One example is described below with reference to FIG. 6B.

Figure 5:
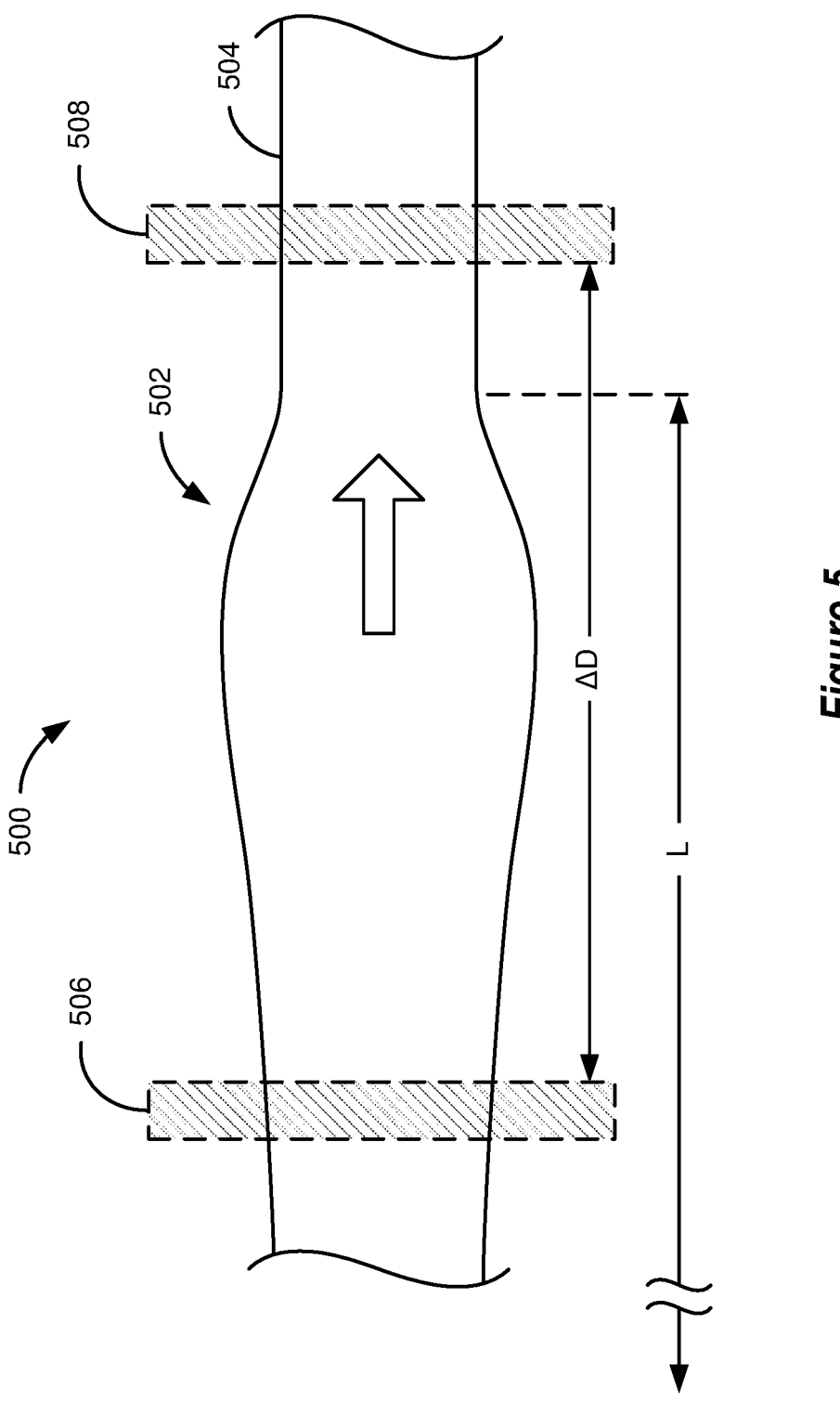
FIG. 5 shows a cross-sectional side view of a diagrammatic representation of a portion of an artery through which a pulse is propagating.

FIG. 5 shows a cross-sectional side view of a diagrammatic representation of a portion of an artery 500 through which a pulse 502 is propagating. The block arrow in FIG. 5 shows the direction of blood flow and pulse propagation. As diagrammatically shown, the propagating pulse 502 causes strain in the arterial walls 504, which is manifested in the form of an enlargement in the diameter (and consequently the cross-sectional area) of the arterial walls— referred to as "distension." The spatial length L of an actual propagating pulse along an artery (along the direction of blood flow) is typically comparable to the length of a limb, such as the distance from a subject's shoulder to the subject's wrist or finger, and is generally less than one meter (m). However, the length L of a propagating pulse can vary considerably from subject to subject, and for a given subject, can vary significantly over durations of time depending on various factors. The spatial length L of a pulse will generally decrease with increasing distance from the heart until the pulse reaches capillaries.

As described above, some particular implementations relate to devices, systems and methods for estimating blood pressure or other cardiovascular characteristics based on estimates of an arterial distension waveform. The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein. In some implementations, the pulse wave velocity (PWV) of a propagating pulse may be estimated by measuring the pulse transit time (PTT) of the pulse as it propagates from a first physical location along an artery to another more distal second physical location along the artery. However, either version of the PTT may be used for the purpose of blood pressure estimation. Assuming that the physical distance $\Delta D$ between the first and the second physical locations is ascertainable, the PWV can be estimated as the quotient of the physical spatial distance $\Delta D$ traveled by the pulse divided by the time (PTT) the pulse takes in traversing the physical spatial distance $\Delta D$. Generally, a first sensor positioned at the first physical location is used to determine a starting time (also referred to herein as a "first temporal location") at which point the pulse arrives at or propagates through the first physical location. A second sensor at the second physical location is used to determine an ending time (also referred to herein as a "second temporal location") at which point the pulse arrives at or propagates through the second physical location and continues through the remainder of the arterial branch. In such examples, the PTT represents the temporal distance (or time difference) between the first and the second temporal locations (the starting and the ending times).

The fact that measurements of the arterial distension waveform are performed at two different physical locations implies that the estimated PWV inevitably represents an average over the entire path distance $\Delta D$ through which the pulse propagates between the first physical location and the second physical location. More specifically, the PWV generally depends on a number of factors including the density of the blood p, the stiffness E of the arterial wall (or inversely the elasticity), the arterial diameter, the thickness of the arterial wall, and the blood pressure. Because both the arterial wall elasticity and baseline resting diameter (for example, the diameter at the end of the ventricular diastole period) vary significantly throughout the arterial system, PWV estimates obtained from PTT measurements are inherently average values (averaged over the entire path length $\Delta D$ between the two locations where the measurements are performed).

In traditional methods for obtaining PWV, the starting time of the pulse has been obtained at the heart using an electrocardiogram (ECG) sensor, which detects electrical signals from the heart. For example, the starting time can be estimated based on the QRS complex—an electrical signal characteristic of the electrical stimulation of the heart ventricles. In such approaches, the ending time of the pulse is typically obtained using a different sensor positioned at a second location (for example, a finger). As a person having ordinary skill in the art will appreciate, there are numerous arterial discontinuities, branches, and variations along the entire path length from the heart to the finger. The PWV can change by as much as or more than an order of magnitude along various stretches of the entire path length from the heart to the finger. As such, PWV estimates based on such long path lengths are unreliable.

In various implementations described herein, PTT estimates are obtained based on measurements (also referred to as "arterial distension data" or as "an acoustic wave corresponding to a photoacoustic response") associated with an arterial distension signal obtained by each of a first arterial distension sensor 506 and a second arterial distension sensor 508 proximate first and second physical locations, respectively, along an artery of interest. In some particular implementations, the first arterial distension sensor 506 and the second arterial distension sensor 508 are advantageously positioned proximate first and second physical locations between which arterial properties of the artery of interest, such as wall elasticity and diameter, can be considered or assumed to be relatively constant. In this way, the PWV calculated based on the PTT estimate is more representative of the actual PWV along the particular segment of the artery. In turn, the blood pressure P estimated based on the PWV is more representative of the true blood pressure. In some implementations, the magnitude of the distance $\Delta D$ of separation between the first arterial distension sensor 506 and the second arterial distension sensor 508 (and consequently the distance between the first and the second locations along the artery) can be in the range of about 1 centimeter (cm) to tens of centimeters-long enough to distinguish the arrival of the pulse at the first physical location from the arrival of the pulse at the second physical location, but close enough to provide sufficient assurance of arterial consistency. In some specific implementations, the distance ΔD between the first and the second arterial distension sensors 506 and 508 can be in the range of about 1 cm to about 30 cm, and in some implementations, less than or equal to about 20 cm, and in some implementations, less than or equal to about 10 cm, and in some specific implementations less than or equal to about 5 cm. In some other implementations, the distance ΔD between the first and the second arterial distension sensors 506 and 508 can be less than or equal to 1 cm, for example, about 0.1 cm, about 0.25 cm, about 0.5 cm or about 0.75 cm. By way of reference, a typical PWV can be about 15 meters per second (m/s). Using a monitoring device in which the first and the second arterial distension sensors 506 and 508 are separated by a distance of about 5 cm, and assuming a PWV of about 15 m/s implies a PTT of approximately 3.3 milliseconds (ms).

The value of the magnitude of the distance ΔD between the first and the second arterial distension sensors 506 and 508, respectively, can be preprogrammed into a memory within a monitoring device that incorporates the sensors (for example, such as a memory of, or a memory configured for communication with a control system such as 706 that is described below with reference to FIG. 7). As will be appreciated by a person of ordinary skill in the art, the spatial length L of a pulse can be greater than the distance ΔD from the first arterial distension sensor 506 to the second arterial distension sensor 508 in such implementations. As such, although the diagrammatic pulse 502 shown in FIG. 5 is shown as having a spatial length L comparable to the distance between the first arterial distension sensor 506 and the second arterial distension sensor 508, in actuality each pulse can typically have a spatial length L that is greater and even much greater than (for example, about an order of magnitude or more than) the distance ΔD between the first and the second arterial distension sensors 506 and 508.

In some implementations of the monitoring devices disclosed herein, both the first arterial distension sensor 506 and the second arterial distension sensor 508 are sensors of the same sensor type. In some such implementations, the first arterial distension sensor 506 and the second arterial distension sensor 508 are identical sensors. In such implementations, each of the first arterial distension sensor 506 and the second arterial distension sensor 508 utilizes the same sensor technology with the same sensitivity to the arterial distension signal caused by the propagating pulses, and has the same time delays and sampling characteristics. In some implementations, each of the first arterial distension sensor 506 and the second arterial distension sensor 508 is configured for photoacoustic plethysmography (PAPG) sensing, e.g., as disclosed elsewhere herein. Some such implementations include a light source system and two or more ultrasonic receivers. In some implementations, each of the first arterial distension sensor 506 and the second arterial distension sensor 508 is configured for ultrasound sensing via the transmission of ultrasonic signals and the receipt of corresponding reflections. In some alternative implementations, each of the first arterial distension sensor 506 and the second arterial distension sensor 508 may be configured for impedance plethysmography (IPG) sensing, also referred to in biomedical contexts as bioimpedance sensing. In various implementations, whatever types of sensors are utilized, each of the first and the second arterial distension sensors 506 and 508 broadly functions to capture and provide arterial distension data indicative of an arterial distension signal resulting from the propagation of pulses through a portion of the artery proximate to which the respective sensor is positioned. For example, the arterial distension data can be provided from the sensor to a processor in the form of voltage signal generated or received by the sensor based on an ultrasonic signal or an impedance signal sensed by the respective sensor.

As described above, during the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

In the context of bioimpedance sensing (or impedance plethysmography), the blood in the arteries has a greater electrical conductivity than that of the surrounding or adjacent skin, muscle, fat, tendons, ligaments, bone, lymph or other tissues. The susceptance (and thus the permittivity) of blood also is different from the susceptances (and permittivities) of the other types of surrounding or nearby tissues. As a pulse propagates through a particular location, the corresponding increase in the volume of blood results in an increase in the electrical conductivity at the particular location (and more generally an increase in the admittance, or equivalently a decrease in the impedance). Conversely, during the diastolic phase of the cardiac cycle, the corresponding decrease in the volume of blood results in an increase in the electrical resistivity at the particular location (and more generally an increase in the impedance, or equivalently a decrease in the admittance).

A bioimpedance sensor generally functions by applying an electrical excitation signal at an excitation carrier frequency to a region of interest via two or more input electrodes, and detecting an output signal (or output signals) via two or more output electrodes. In some more specific implementations, the electrical excitation signal is an electrical current signal injected into the region of interest via the input electrodes. In some such implementations, the output signal is a voltage signal representative of an electrical voltage response of the tissues in the region of interest to the applied excitation signal. The detected voltage response signal is influenced by the different, and in some instances time-varying, electrical properties of the various tissues through which the injected excitation current signal is passed. In some implementations in which the bioimpedance sensor is operable to monitor blood pressure, heartrate or other cardiovascular characteristics, the detected voltage response signal is amplitude- and phase-modulated by the time-varying impedance (or inversely the admittance) of the underlying arteries, which fluctuates synchronously with the user's heartbeat as described above. To determine various biological characteristics, information in the detected voltage response signal is generally demodulated from the excitation carrier frequency component using various analog or digital signal processing circuits, which can include both passive and active components.

In some examples incorporating ultrasound sensors, measurements of arterial distension may involve directing ultrasonic waves into a limb towards an artery, for example, via one or more ultrasound transducers. Such ultrasound sensors also are configured to receive reflected waves that are based, at least in part, on the directed waves. The reflected waves may include scattered waves, specularly reflected waves, or both scattered waves and specularly reflected waves. The reflected waves provide information about the arterial walls, and thus the arterial distension.

In some implementations, regardless of the type of sensors utilized for the first arterial distension sensor 506 and the second arterial distension sensor 508, both the first arterial distension sensor 506 and the second arterial distension sensor 508 can be arranged, assembled or otherwise included within a single housing of a single monitoring device. As described above, the housing and other components of the monitoring device can be configured such that when the monitoring device is affixed or otherwise physically coupled to a subject, both the first arterial distension sensor 506 and the second arterial distension sensor 508 are in contact with or in close proximity to the skin of the user at first and second locations, respectively, separated by a distance ΔD, and in some implementations, along a stretch of the artery between which various arterial properties can be assumed to be relatively constant. In various implementations, the housing of the monitoring device is a wearable housing or is incorporated into or integrated with a wearable housing. In some specific implementations, the wearable housing includes (or is connected with) a physical coupling mechanism for removable non-invasive attachment to the user. The housing can be formed using any of a variety of suitable manufacturing processes, including injection molding and vacuum forming, among others. In addition, the housing can be made from any of a variety of suitable materials, including, but not limited to, plastic, metal, glass, rubber and ceramic, or combinations of these or other materials. In particular implementations, the housing and coupling mechanism enable full ambulatory use. In other words, some implementations of the wearable monitoring devices described herein are noninvasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the monitoring device facilitates and enables long-term wearing and monitoring (for example, over days, weeks or a month or more without interruption) of one or more biological characteristics of interest to obtain a better picture of such characteristics over extended durations of time, and generally, a better picture of the user's health.

Figure 6A:
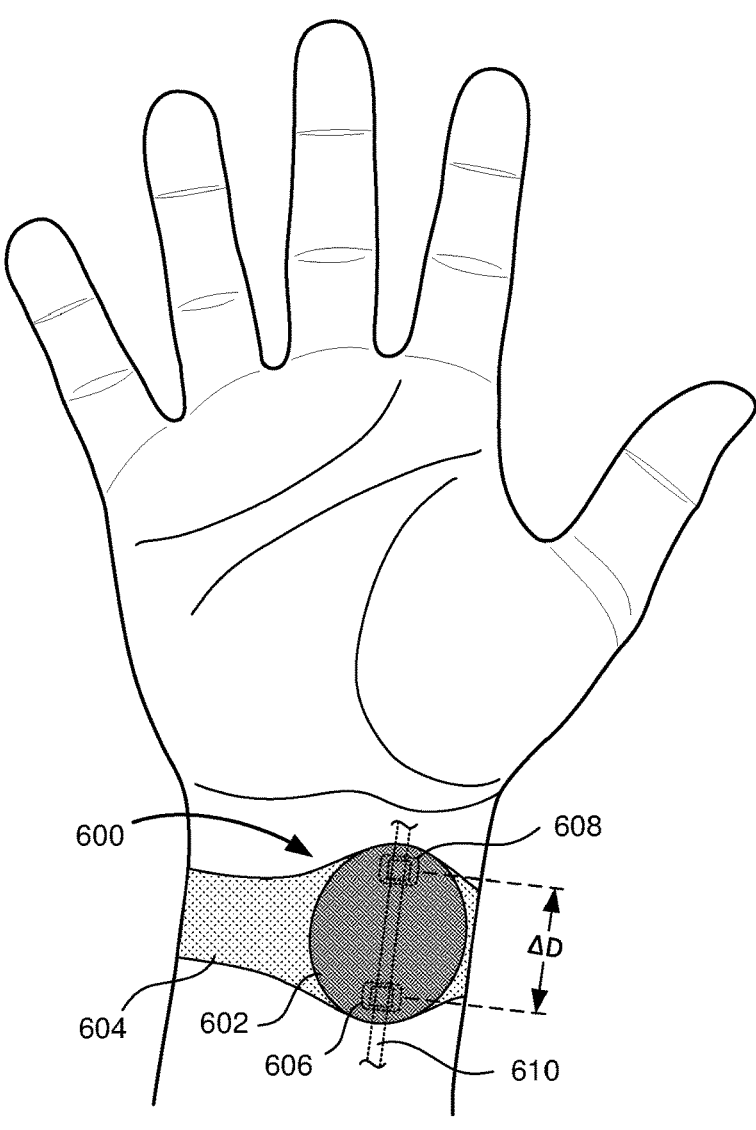
FIG. 6A shows an example monitoring device designed to be worn around a wrist according to some implementations.

In some implementations, the monitoring device can be positioned around a wrist of a user with a strap or band, similar to a watch or fitness/activity tracker. FIG. 6A shows an example monitoring device 600 designed to be worn around a wrist according to some implementations. In the illustrated example, the monitoring device 600 includes a housing 602 integrally formed with, coupled with or otherwise integrated with a wristband 604. The first and the second arterial distension sensors 606 and 608 may, in some instances, each include an instance of the ultrasonic receiver system and a portion of the light source system that are described above. In this example, the monitoring device 600 is coupled around the wrist such that the first and the second arterial distension sensors 606 and 608 within the housing 602 are each positioned along a segment of the radial artery

610 (note that the sensors are generally hidden from view from the external or outer surface of the housing facing the subject while the monitoring device is coupled with the subject, but exposed on an inner surface of the housing to enable the sensors to obtain measurements through the subject's skin from the underlying artery). Also as shown, the first and the second arterial distension sensors 606 and 608 are separated by a fixed distance ΔD. In some other implementations, the monitoring device 600 can similarly be designed or adapted for positioning around a forearm, an upper arm, an ankle, a lower leg, an upper leg, or a finger (all of which are hereinafter referred to as "limbs") using a strap or band.

Figure 6B:
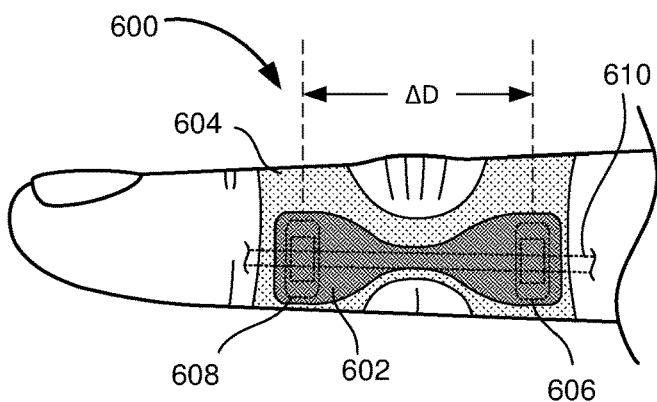
FIG. 6B shows an example monitoring device designed to be worn on a finger according to some implementations.

FIG. 6B shows an example monitoring device 600 designed to be worn on a finger according to some implementations. The first and the second arterial distension sensors 606 and 608 may, in some instances, each include an instance of the ultrasonic receiver and a portion of the light source system that are described above.

In some other implementations, the monitoring devices disclosed herein can be positioned on a region of interest of the user without the use of a strap or band. For example, the first and the second arterial distension sensors 606 and 608 and other components of the monitoring device can be enclosed in a housing that is secured to the skin of a region of interest of the user using an adhesive or other suitable attachment mechanism (an example of a "patch" monitoring device).

Figure 6C:
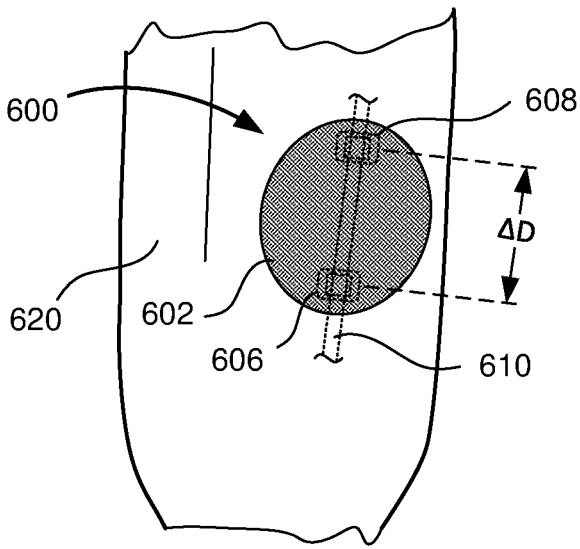
FIG. 6C shows an example monitoring device designed to reside on an earbud according to some implementations.

FIG. 6C shows an example monitoring device 600 designed to reside on an earbud according to some implementations. According to this example, the monitoring device 600 is coupled to the housing of an earbud 620. The first and second arterial distension sensors 606 and 608 may, in some instances, each include an instance of the ultrasonic receiver and a portion of the light source system that are described above.

Figure 7:
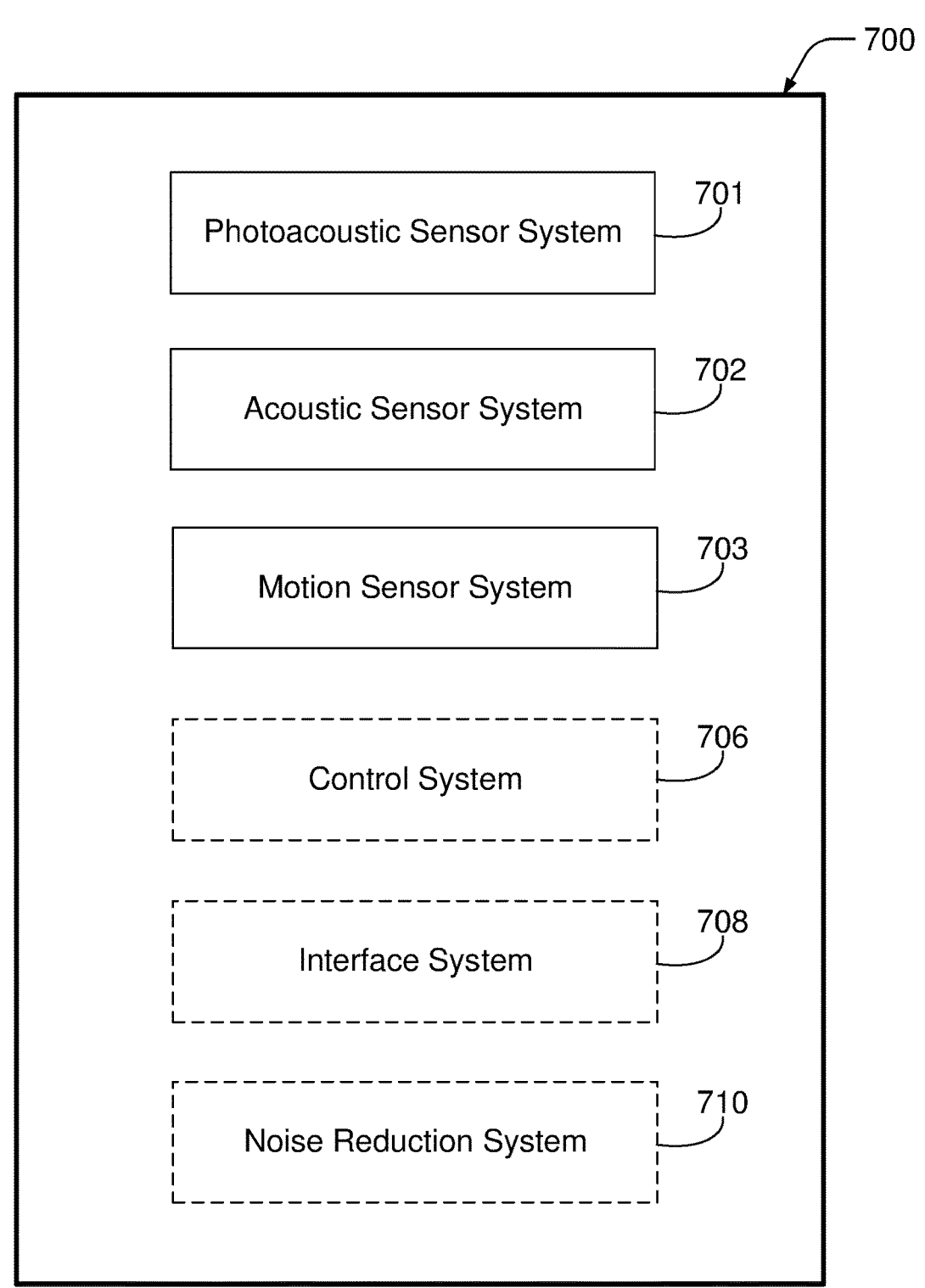
FIG. 7 is a block diagram that shows example components of a PAPG-based apparatus according to some disclosed implementations.

FIG. 7 is a block diagram that shows example components of a PAPG-based apparatus 700 according to some disclosed implementations. The apparatus 700 may comprise a single device or a group of interconnected devices. The apparatus 700 may correspond with or all of the components of the devices illustrated in FIGS. 4-6C. In this example, the apparatus 700 may include a photoacoustic sensor system 701, an acoustic sensor system 702, and a motion sensor system 703. Optionally (as shown by dashed lines), some implementations of the apparatus 700 may include a control system 706, an interface system 708, a noise reduction system 710, or combinations thereof. In specific implementations, the interface system 708 (including, e.g., a contact surface) may be included so as to allow contact with skin to maximize the sensitivity of the acoustic sensor system 702 and/or the motion sensor system 703.

In some embodiments, the photoacoustic sensor system 701 may include an interface, a light source system, a receiver system, and may be an example of the blood pressure monitoring device based on PAPG as described previously. In some implementations, the photoacoustic sensor system 701 may also include a controller system or a controller.

Some disclosed PAPG sensors described herein (such as photoacoustic sensor system 701) may include a platen, a light source system, and an ultrasonic receiver system. According to some implementations, the light source system may include a light source configured to produce and direct light. In some implementations, the platen may include an anti-reflective layer, a mirror layer, or combinations thereof. According to some implementations, the platen may have an outer surface, or a layer on the outer surface, with an acoustic impedance that is configured to approximate the acoustic impedance of human skin. In some implementations, the platen may have a surface proximate the ultrasonic receiver system, or a layer on the surface proximate the ultrasonic receiver system, with an acoustic impedance that is configured to approximate the acoustic impedance of the ultrasonic receiver system.

Some disclosed PAPG sensors described herein (such as photoacoustic sensor system 701) may include an interface, a light source system and an ultrasonic receiver system. Some such devices may not include a rigid platen. According to some implementations, the interface may be a physical, flexible interface constructed of one or more of suitable materials having a desired property or properties (e.g., an acoustic property such as acoustic impedance, softness of the material). In some implementations, the interface may be a flexible interface that can contact a target object that may be proximate to or contact the interface. There may be salient differences between such an interface and a platen. In some implementations, the light source system may be configured to direct light using one or more optical waveguides (e.g., optical fibers) configured to direct light toward a target object. According to some implementations, the interface may have an outer surface, or a layer on the outer surface, with an acoustic impedance that is configured to approximate the acoustic impedance of human skin. Such outer surface may have a contact portion that is contactable by a user or a body part of the user (e.g., finger, wrist). In some examples, the optical waveguide(s) may be embedded in one or more acoustic matching layers that are configured to bring the light transmitted by the optical waveguide(s) very close to tissue. The outer surface and/or other parts of the interface may be compliant, pliable, flexible, or otherwise at least partially conforming to the shape and contours of the body part of the user. In some implementations, the interface may have a surface proximate the ultrasonic receiver system, or a layer on the surface proximate the ultrasonic receiver system, with an acoustic impedance that is configured to approximate the acoustic impedance of the ultrasonic receiver system. According to some examples, the receiver system may be, or may include, an ultrasonic receiver array. In some examples, the photoacoustic sensor system 701 may include one or more separate ultrasonic transmitter elements or one or more separate arrays of ultrasonic transmitter elements. In some examples, the ultrasonic transmitter(s) may include an ultrasonic plane-wave generator.

In some implementations, at least portions of the photoacoustic sensor system 701 (for example, the receiver system, the light source system, or both) may include one or more sound-absorbing layers, acoustic isolation material, light-absorbing material, light-reflecting material, or combinations thereof. In some examples, acoustic isolation material may reside between the light source system and at least a portion of the receiver system. In some examples, at least portions of the photoacoustic sensor system 701 (for example, the receiver system, the light source system, or both) may include one or more electromagnetically shielded transmission wires. In some such examples, the one or more electromagnetically shielded transmission wires may be configured to reduce electromagnetic interference from the light source system that is received by the receiver system.

The controller control system 706 may include one or more general purpose single- or multi-chip processors, digital signal processors (DSPs), application specific integrated circuits (ASICs), field programmable gate arrays (FPGAs)

or other programmable logic devices, discrete gates or transistor logic, discrete hardware components, or combinations thereof. The control system 706 also may include (and/or be configured for communication with) one or more memory devices, such as one or more random access memory (RAM) devices, read-only memory (ROM) devices, etc. Accordingly, the photoacoustic sensor system 701 may have a memory system that includes one or more memory devices. The control system 706 may be configured for receiving and processing data from the receiver system, e.g., as described below. If the photoacoustic sensor system 701 includes an ultrasonic transmitter, the control system 706 may be configured for controlling the ultrasonic transmitter. In some implementations, functionality of the control system 706 may be partitioned between one or more controllers or processors, such as a dedicated sensor controller and an applications processor of a mobile device.

In some examples, the control system 706 may be communicatively coupled to the light source system and configured to control the light source system to emit light towards a target object on an outer surface of the interface. In some such examples, the control system 706 may be configured to receive signals from the ultrasonic receiver system corresponding to the ultrasonic waves generated by the target object responsive to the light from the light source system. In some examples, the control system 706 may be configured to identify one or more blood vessel signals, such as arterial signals or vein signals, from the ultrasonic receiver system. In some such examples, the one or more arterial signals or vein signals may be, or may include, one or more blood vessel wall signals corresponding to ultrasonic waves generated by one or more arterial walls or vein walls of the target object. In some such examples, the one or more arterial signals or vein signals may be, or may include, one or more arterial blood signals corresponding to ultrasonic waves generated by blood within an artery of the target object or one or more vein blood signals corresponding to ultrasonic waves generated by blood within a vein of the target object.

In some examples, the control system 706 may be configured to determine or estimate one or more physiological parameters or cardiac features based, at least in part, on one or more arterial signals, on one or more vein signals, or on combinations thereof. According to some examples, the cardiac features may be, or may include, blood pressure. In some embodiments, the control system 706 may use the data from the photoacoustic sensor system 701 along with data from other components of the apparatus 700, e.g., the acoustic sensor system 702 and the motion sensor system 703 to determine enhanced physiological parameters according to various embodiments described herein.

In further examples, the control system 706 may be communicatively coupled to the receiver system. The receiver system may be configured to detect acoustic signals from the target object. The control system 706 may be configured to select at least one of a plurality of receiver elements of the receiver system. Such selected receiver element(s) may correspond to the best signals from multiple receiver elements. In some embodiments, the selection of the at least one receiver element may be based on information regarding detected acoustic signals (e.g., arterial signals or vein signals) from the plurality of receivers. For example, signal quality or signal strength (based, e.g., on signal-to-noise ratio (SNR)) of some signals may be relatively higher than some others or above a prescribed threshold or percentile, which may indicate the best signals. In some implementations, the control system 706 may also be configured to, based on the information regarding detected acoustic signals, determine or estimate at least one characteristic of the blood vessels such as pulse wave velocity (indicative of arterial stiffness), arterial dimensions, or both.

Some implementations of the apparatus 700 may include an interface system 708. In some examples, the interface system 708 may include a wired and/or wireless communication interface system. A communication interface system may allow the apparatus 700 to communicate with other devices for systems. According to some embodiments, in addition or as an alternative to having an integrated motion sensor system 703 by which activity information may be obtained, the apparatus 700 may communicate with one or more other devices, including sensors, which may provide the apparatus 700 with activity information comprising sensor data and/or data derived therefrom (e.g., an identified motion or activity, etc.). Embodiments describing how such activity information may be used are described in more detail hereafter.

In some implementations, the interface system 708 may include a user interface system, one or more network interfaces, one or more interfaces between the control system 706 and a memory system and/or one or more interfaces between the control system 706 and one or more external device interfaces (e.g., ports or applications processors), or combinations thereof. According to some examples in which the interface system 708 is present and includes a user interface system, the user interface system may include a microphone system, a loudspeaker system, a haptic feedback system, a voice command system, one or more displays, or combinations thereof. According to some examples, the interface system 708 may include a touch sensor system, a gesture sensor system, or a combination thereof. The touch sensor system (if present) may be, or may include, a resistive touch sensor system, a surface capacitive touch sensor system, a projected capacitive touch sensor system, a surface acoustic wave touch sensor system, an infrared touch sensor system, any other suitable type of touch sensor system, or combinations thereof.

In some examples, the interface system 708 may include a force sensor system. The force sensor system (if present) may be, or may include, a piezo-resistive sensor, a capacitive sensor, a thin film sensor (for example, a polymer-based thin film sensor), another type of suitable force sensor, or combinations thereof. If the force sensor system includes a piezo-resistive sensor, the piezo-resistive sensor may include silicon, metal, polysilicon, glass, or combinations thereof. An ultrasonic fingerprint sensor and a force sensor system may, in some implementations, be mechanically coupled. In some implementations, the force sensor system may be mechanically coupled to a platen. In some such examples, the force sensor system may be integrated into circuitry of the ultrasonic fingerprint sensor. In some examples, the interface system 708 may include an optical sensor system, one or more cameras, or a combination thereof.

According to some examples, the apparatus 700 may include a noise reduction system 710. For example, the noise reduction system 710 may include one or more mirrors that are configured to reflect light from the light source system away from the receiver system. In some implementations, the noise reduction system 710 may include one or more sound-absorbing layers, acoustic isolation material, light-absorbing material, light-reflecting material, or combinations thereof. In some examples, the noise reduction system 710 may include acoustic isolation material, which may reside between the light source system and at least a portion of the receiver system, on at least a portion of the receiver system, or combinations thereof. In some examples, the noise reduction system 710 may include one or more electromagnetically shielded transmission wires. In some such examples, the one or more electromagnetically shielded transmission wires may be configured to reduce electromagnetic interference from circuitry of the light source system, receiver system circuitry, or combinations thereof, that is received by the receiver system.

The motion sensor system 703 may comprise one or more motion sensors that can be used, for example, to obtain activity information, according to some embodiments. Apple, the motion sensor system 703 may comprise one or more accelerometers, gyroscopes, altimeters, and/or other inertial or motion sensors capable of determining movement of the artist 700 and/or one or more devices communicatively coupled therewith. According to some embodiments, the motion sensor system 703 could also be used to obtain additional information about tissue motion, cancel environmental noise or motion, and improve signal quality and enhance physiological measurements relating to heart rate, blood pressure, etc.

The apparatus 700 may be used in a variety of different contexts, many examples of which are disclosed herein. For example, in some implementations a mobile device may include the photoacoustic sensor system 701, the acoustic sensor system 702, and the motion sensor system 703. In some such examples, the mobile device may be a smart phone. In some implementations, a wearable device may include the photoacoustic sensor system 701, the acoustic sensor system 702, and the motion sensor system 703. The wearable device may, for example, be a bracelet, an armband, a wristband, a watch, a ring, a headband or a patch. In certain embodiments, the wearable device may be one or a pair of earbuds, a headset, a head rest mount, a headband, headphones, or another head-wearable or head-mounted device. An example monitoring device designed to reside on an earbud is shown in FIG. 6C.

As previously noted, a PAPG device (e.g., apparatus 700) may be capable of determining blood pressure and other physiological measurements using PAPG measurements alone. For example, a model that correlates PAPG measurements (e.g., PTT, PWV) to blood pressure can be used to determine a blood pressure estimate corresponding to PAPG measurements. However, the use of such a model as its limitations because each user may have a different correlation between PAPG measurements and blood pressure. Accordingly, a "one model fits all" BP estimation can be further improved with personalization. This personalization can be implemented via machine learning (ML) (e.g., deep learning) models. But this personalization may be limited based on PAPG measurement information. Additional information such as an individual's various lifestyle choices, physical activities, sleep, resting heart rate (HR), or the like, can help with personalization and ultimately ensure a more accurate blood pressure estimate.

As described herein, a "model" may characterize a correlation between a PAPG measurement and blood pressure. Generally speaking, these correlation models may be represented by curves in a plot of blood pressure over a particular PAPG measurement (e.g., PWV), and a personalized model may represent a curve that is personalized to a particular user of the PAPG device. Such models may therefore enable accurate blood pressure to be estimated using the correlation between blood pressure and PAPG measurements for a particular user.

With this in mind, embodiments herein are directed toward obtaining and utilizing activity information to determine a model, personalized to an individual, that can be used to accurately determine blood pressure estimates by a PAPG device (e.g., a wearable device as previously described) based on PAPG measurement information. Depending on desired functionality, embodiments may implement different techniques to provide for utilizing activity information to enhance blood pressure estimates. For example, according to a first technique (described in more detail below with respect to FIG. 8) activity information obtained over time may be utilized to personalize a general model in the general manner described above. According to a second technique (described in more detail below with respect to FIG. 9), a calibration process may be performed during which a well calibrated device performs blood pressure measurements while the user performs different activities and the PAPG device or other device(s) (e.g., microphone, piezoelectric device, EKG in combination with PAPG/oscillometric techniques) obtains measurements, enabling the selection and subsequent use of a model that accurately correlates PAPG measurements with blood pressure.

Figure 8:
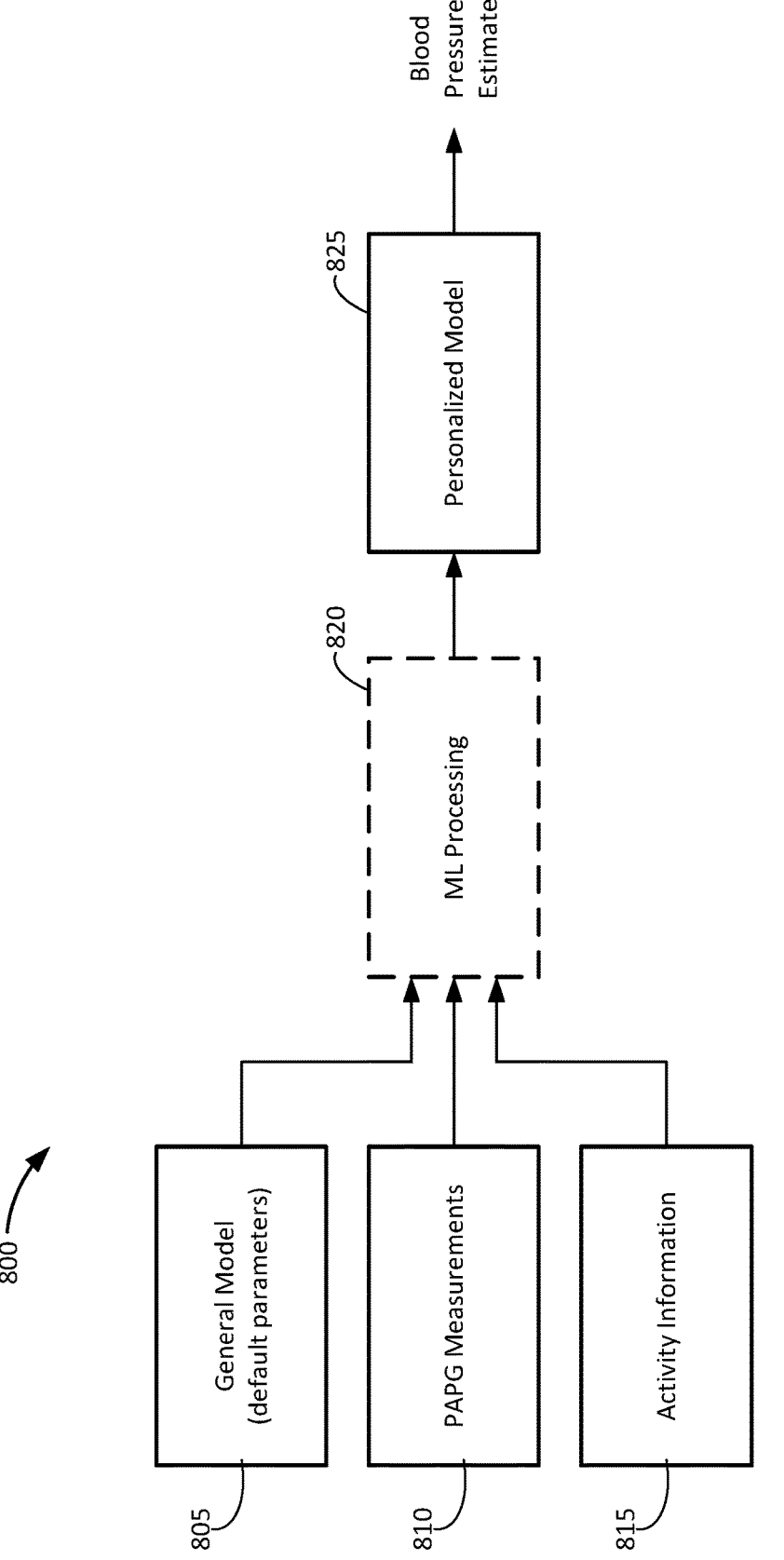
FIG. 8 is a block diagram that illustrates a first technique of utilizing activity information to enhance blood pressure estimates, according to some disclosed implementations.

FIG. 8 is a block diagram 800 that illustrates the first technique, in which a general model 805 is personalized to a particular user based not only on PAPG measurements 810, but also on activity information 815 regarding activities performed by the particular user. As noted, this personalization may be performed by ML processing 820 (e.g., a deep learning ML model), which can modify the general model 805 to provide a personalized model 825, as illustrated. The personalized model 825 can then be used to obtain a more accurate blood pressure estimate for the particular user.

The general model 805 may comprise an initial correlation model used to correlate PAPG measurements with blood pressure. Depending on desired functionality, the general model 805 may comprise a model that performs well across various demographics, enabling relatively accurate modeling for various types of users. According to some embodiments, the general model 805 may be "tuned" using one or more features (not shown) that may be correlated with blood pressure, such as age, health, weight, etc. These features may be input, for example, by a user via a user interface (e.g., which may be part of interface system 708, as previously described).

The ML processing 820 may generate the personalized model 825 by performing additional tuning based on PAPG measurements 810 and activity information 815, which can increase the accuracy of blood pressure estimates. That is, the personalized model 825 can be used to accurately estimate blood pressure for a particular user based at least in part on knowledge of various activities (e.g., exercise, sleep, etc.) engaged in by the user. More specifically, according to some embodiments, the activity information 815 may be obtained while the user undergoes various activities, which can enable ML processing 820 to perform additional and/or enhanced tuning (e.g., compared with tuning based on PAPG measurements 810 and/or initial tuning of the general model 805 alone). This additional/enhanced tuning and result in a more personalized model 825 that can provide a more accurate blood pressure estimate. Depending on desired functionality, the tuning of a model may involve updating weights for individual features derived from PAPG signals and/or determining which correlated features (e.g., health, age, etc.) to use and/or weigh for particular individual. According to some embodiments, activity information 815 may be correlated with PAPG measurements 810 to determine certain features (e.g., resting heart rate (HR) that may be used to tune the personalized model 825.

To be clear, such personalization may be ongoing. That is, the ML processing 820 may continuously tune the personalized model 825 based on activity information 815 obtained over time. Moreover, according to some embodiments, daily and/or long-term (e.g., historical) activity information can be used as an added feature in the personalized model 825. The personalized model 825 can then be used to determine a blood pressure estimate based on PAPG measurements 810 (which may or may not be performed during a particular activity). Depending on implementation, a PAPG device may not be able to obtain PAPG measurements 810 during some activities. However, recent and/or historical activity information used to tune the personalized model 825 and therefore may be accounted for when determining a blood pressure estimate based on PAPG measurements 810.

The source(s) and/or content of the activity information 815 may vary, depending on desired functionality. As noted elsewhere herein, the activity information 815 may be obtained via (i) sensors and/or systems incorporated into a PAPG device (e.g., motion sensor system 703) and/or (ii) one or more sources (e.g., sensors, systems, devices) separate from, but communicatively coupled with, the PAPG device. These one or more sources may comprise separate wearable devices worn by the user of the PAPG device. Activity trackers and/or smartwatches, for example, may comprise devices separate from a PAPG device that may be capable of providing the PAPG device with the activity information 815 used to generate the personalized model 825.

With respect to the content, the activity information 815 may comprise sensor data (e.g., from accelerometers, altimeters, gyrometers/gyroscopes, IMUs, etc.) and/or higher-level information derived therefrom. Higher-level information may include the identification of a specific activity (e.g., jogging, walking, biking, sleeping, etc.), the identification of a category or type of activity (e.g., high-paced or low-paced activity, exercise or non-exercise, etc.), or a combination thereof. Higher-level information may be provided, for example, in cases where a separate wearable (e.g., activity tracker, smartwatch, etc.) determines an activity or activity type based on raw sensor information. According to some embodiments, indicative of an intensity of the activity may also be provided. A running speed, for example, may be included in activity information 815 indicative of running.

It can be noted that, PAPG measurements 810 may be indicative of activities and may be used to provide activity information 815, in some embodiments. However, other embodiments may use activity information 815 comprising non-PAPG measurements to provide additional data to the ML processing 820 of the personalized model 825. Because PAPG measurements 810 may be impacted by factors other than activities (e.g., heat, stress, etc.), the use of activity information 815 comprising non-PAPG measurements can help ensure the data is indicative of a particular activity or activity type.

Figure 9:
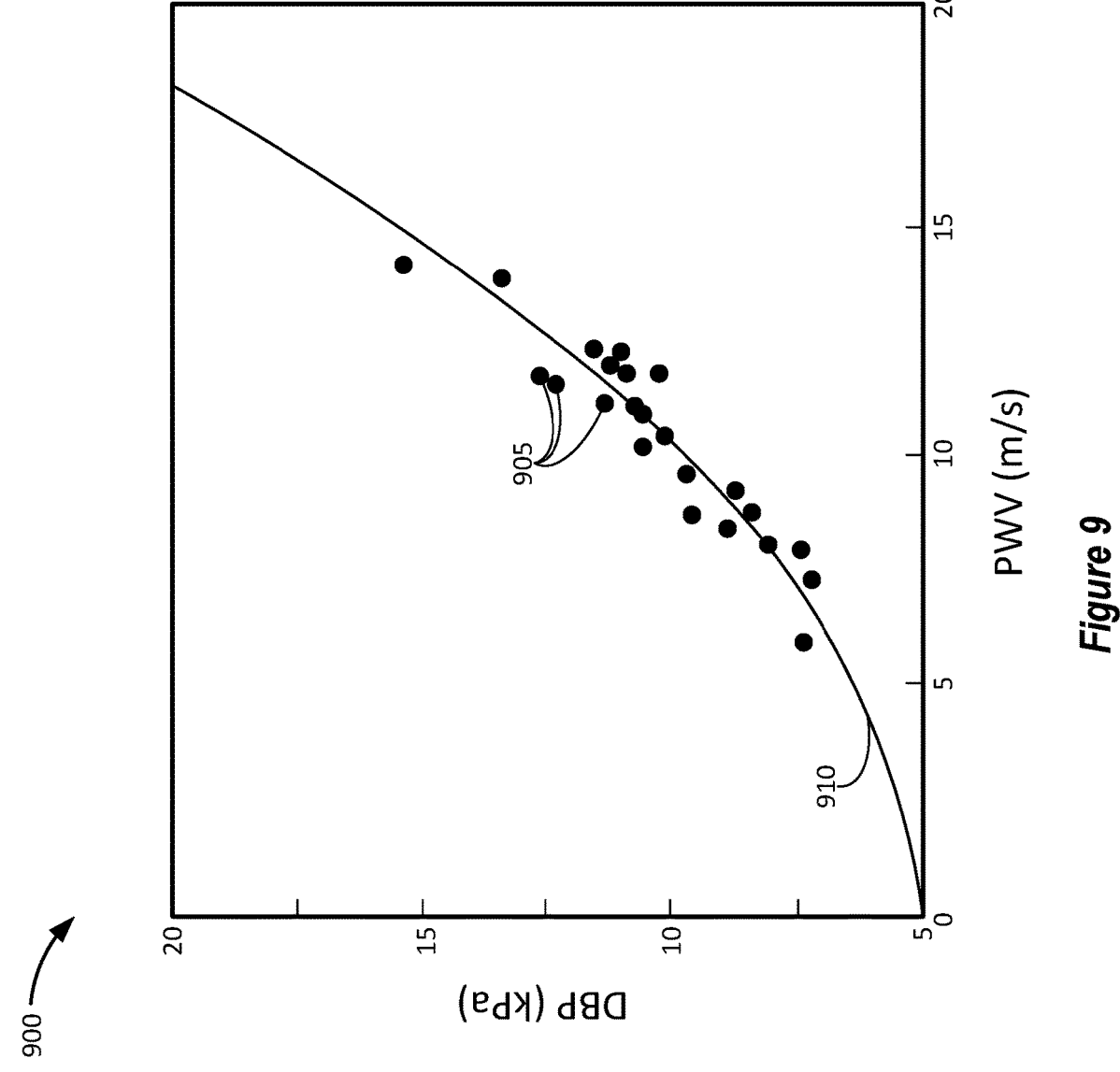
FIG. 9 is a block diagram used to illustrate a second technique of utilizing activity information to enhance blood pressure estimates, according to some disclosed implementations.

FIG. 9 is an example graph 900 that illustrates the second technique, in which a calibration process may be performed to determine a model that accurately correlates PAPG measurements with blood pressure for a particular user. According to this technique, accurate non-PAPG blood pressure measurements (which serve as ground truth measurements of blood pressure) may be performed during the calibration process using a well-calibrated device while the user performs a variety of activities. The PAPG device may obtain PAPG measurements concurrently, and the correlation between the non-PAPG blood pressure measurements can result in data points 905 that can be used to determine a model 910 that may be used to correlate PAPG measurements with blood pressure. Once the model 910 is determined, the PAPG device may then be used (subsequent to the calibration process) determine an accurate blood pressure estimate based on PAPG measurements, which are typically less invasive than the non-PAPG blood pressure measurements used in the calibration process to determine the model 910.

The non-PAPG blood pressure measurements may be performed, for example, using oscillometry and/or an electrocardiogram (EKG). Depending on implementation, this information may be obtained by the PAPG device (e.g., if it has oscillometry and/or EKG capabilities) and/or a separate device. In some embodiments, the separate device may be communicatively coupled with the PAPG device and may provide the non-PAPG blood pressure measurements directly to the PAPG device (e.g., via a wired or wireless connection). Additionally or alternatively, a user may provide user input comprising the non-PAPG blood pressure measurements via a user interface.

Depending on desired functionality, a user of the PAPG device may be prompted during the calibration process to engage in various activities. For example, using a visual or audio prompt via a user interface, the PAPG device may prompt the user (wearer the PAPG device) to engage in various activities such as sitting, standing, running, walking etc. these various activities can be selected such that blood pressure and other vitals (e.g., PWV) vary significantly. The non-PAPG blood pressure measurements and PAPG measurements (e.g., PWV, PTT) are obtained, resulting in data points 905 from which a model 910 may be determined. According to some embodiments, the PAPG device may continue to prompt a user to engage in various activities until the variation of data points 905 is sufficient enough to allow the determination of the model 910.

According to some embodiments, the determination of the model 910 may be made by an ML or fitting process to select a model from a plurality of candidate models, based on model that fits best with the data points 905. According to some embodiments, the plurality of candidate models may comprise, for example, one or more of:

the Moens–Korteweg or Bramwell–Hill model: $BP = A * \ln(PTT) + B$, the inverse square model: $BP = A/(PTT)^2 + B$, the inverse model: $BP = A/(PTT) + B$, the linear models: $BP = A(PTT) + B$, or the Fungs hyperelastic model: $BP = A * PWV^2 + B$.

With respect to the above models, BP is blood pressure, and A and B are fitting parameters associated with arterial wall stiffness. As with the models themselves, A and B vary are personalized features that vary from individual to individual. The calibration and fitting processes not only can result in the selection of which model to use, but also the determination of values for A and B. According to some embodiments, information in addition to the measurements taken during the calibration process may be used for determination/selection of the model 910. This information can include, for example, age, weight, health, and/or other information which may be known to have a correlation with certain models.

It can be noted that, according to some embodiments, recalibration (e.g., the re-execution of the calibration process) can be performed when a triggering event occurs, where the triggering event is indicative of the need for recalibration. A triggering event may comprise the passage of a threshold amount of time since its previous calibration. This threshold amount of time may be based on known drift in calibrated sensor(s), changes in age factors (e.g., the user's age changing a threshold amount), or the like. Additional triggering events may comprise changes in other factors correlated with blood pressure (e.g., weight, health, etc.), or the like. These triggering events may be determined based on user input, time since input, or the like.

FIG. 10 is a flow diagram of a method 1000 of augmenting a personalized blood pressure model using activity monitoring, according to an embodiment. Means for performing the functionality illustrated in one or more of the blocks shown in FIG. 10 may be performed by hardware and/or software components of a PAPG device or similar apparatus. Example components of a PAPG device are illustrated in FIG. 7, described above.

At block 1010, the functionality comprises obtaining activity information indicative of an activity performed by a person. As noted above (e.g., with respect to FIG. 8), a person may comprise an apparatus user as described elsewhere herein. More specifically, the person may comprise a wearer of the PAPG device (including one or more components of a PAPG device if the PAPG device has more than one component). As also noted in the above-described embodiments, activity information may comprise one or more different types of information. As such, according to some embodiments of the method 1000, the activity information may comprise an identification of the activity, an indication of a category of the activity, sensor data indicative of the activity, or any combination thereof. Additionally, or alternatively, activity information may comprise data obtained from one or more sensors. In such embodiments, these one or more sensors may comprise a gyroscope, an accelerometer, a magnetometer, an altimeter, an inertial measurement unit (IMU), or any combination thereof. As noted above, embodiments may obtain information from one or more sources, which may include systems, devices, sensors, etc., which may be separate from the PAPG device. As such, according to some embodiments of the method 1000, the activity information may be obtained from a device communicatively coupled with the apparatus.

Means for performing functionality at block 1010 may comprise a photoacoustic sensor system 701, acoustic sensor system 702, motion sensor system 703, control system 706, and/or other components of a PAPG device or similar apparatus, as illustrated in FIG. 7.

At block 1020, the functionality comprises updating a model for determining blood pressure of the person based at least in part on the obtained activity information. As noted previously (e.g., with respect to FIG. 8), a model may comprise a correlation model that correlates blood pressure with detected acoustic wave (e.g., PAPG measurement), enabling determination of blood pressure of the person from the detected acoustic wave. According to some embodiments, the model may include a plurality of features correlated to blood pressure. In such embodiments, updating the model may comprise adding one or more features to the plurality of features, subtracting one or more features from the plurality of features, adjusting one or more weights applied to the plurality of features, or any combination thereof. Further, in such embodiments, the plurality of features may include historical activity information. Updating the historical activity information may be based at least in part on the obtained activity information.

Means for performing functionality at block 1020 may comprise a photoacoustic sensor system 701, acoustic sensor system 702, motion sensor system 703, control system 706, and/or other components of a PAPG device or similar apparatus, as illustrated in FIG. 7.

At block 1030, the functionality comprises detecting an acoustic wave corresponding to a photoacoustic response of a blood vessel of the person to light emitted by a light source system. The acoustic wave may comprise a PAPG measurement and/or a PAPG measurement may be derived from the acoustic wave, as described in the embodiments above. As previously noted, a PAPG measurement may comprise a PTT, PWV, HRW, or similar measurements, or any combination thereof.

Means for performing functionality at block 1030 may comprise a photoacoustic sensor system 701, acoustic sensor system 702, motion sensor system 703, control system 706, and/or other components of a PAPG device or similar apparatus, as illustrated in FIG. 7.

At block 1040, the functionality comprises estimating a blood pressure based at least in part on the updated model and the acoustic wave. As noted previously, estimating the blood pressure based on the updated model may be based on a correlation provided by the updated model between the acoustic wave (e.g., PAPG measurement) and a corresponding blood pressure.

Means for performing functionality at block 1040 may comprise a photoacoustic sensor system 701, acoustic sensor system 702, motion sensor system 703, control system 706, and/or other components of a PAPG device or similar apparatus, as illustrated in FIG. 7.

FIG. 11 is a flow diagram of another method 1100 of augmenting a personalized blood pressure model using activity monitoring, according to an embodiment. Means for performing the functionality illustrated in one or more of the blocks shown in FIG. 11 may be performed by hardware and/or software components of a PAPG device or similar apparatus. Example components of a PAPG device are illustrated in FIG. 7, described above.

At block 1120, the functionality comprises obtaining a set of photoacoustic measurements at least in part by detecting acoustic waves corresponding to photoacoustic responses of a blood vessel of a person to light, wherein different photoacoustic measurements of the set of photoacoustic measurements are performed while the person performs a set of activities. The person may comprise an apparatus user, as described herein. As noted above (e.g., with respect to FIG. 9), according to some embodiments, the light may be emitted by a light source system of an apparatus, which may include a light-emitting component. Further, acoustic waves may be detected by a receiver system of the apparatus. As also noted above, the apparatus may prompt the person to engage in various activities of the set of activities to help ensure a sufficient number of blood pressure measurements is taken to determine a model for estimating blood pressure.

Means for performing functionality at block 1120 may comprise a photoacoustic sensor system 701, acoustic sensor system 702, motion sensor system 703, control system 706, and/or other components of a PAPG device or similar apparatus, as illustrated in FIG. 7.

It can be noted that, although a set of photoacoustic measurements may be taken by a PAPG device during calibration (as discussed previously with respect to FIG. 9), embodiments are not so limited. Other devices and/or measurements may be used to enable model determination (at block 1140) and subsequent blood pressure measurements using the determined model. For example, other device(s) may be used to obtain measurements. Additionally or alternatively some measurements (e.g., PWV) can be measured by a number of techniques other than PAPG (e.g., PPG sensor, microphone, piezoelectric device, or a force sensor).

At block 1130, the functionality comprises obtaining a set of reference blood pressure measurements of the person, wherein each reference blood pressure measurement of the set of reference blood pressure measurements corresponds to a respective photoacoustic measurement of the set of photoacoustic measurements. As noted above (e.g., with respect to FIG. 9), the reference blood pressure measurements may be obtained from a well-calibrated device, which may be different than the PAPG device. These reference blood pressure measurements may be used as "ground truth" blood pressure measurements, and may have corresponding photoacoustic measurements that allow a correspondence to be determined (e.g., as illustrated in FIG. 9). According to some embodiments, the reference blood pressure measurements may be obtained from a data source comprising a device communicatively coupled with the apparatus, one or more sensors of the apparatus, or both. According to some embodiments, the data source comprises electrocardiogram (EKG) or oscillometry device. According to some embodiments, blood pressure may be determined using PAPG techniques.

Means for performing functionality at block 1130 may comprise a photoacoustic sensor system 701, acoustic sensor system 702, motion sensor system 703, control system 706, and/or other components of a PAPG device or similar apparatus, as illustrated in FIG. 7.

At block 1140, the functionality comprises determining a model for estimating blood pressure of the person from subsequent photoacoustic measurements based on a correlation between the set of reference blood pressure measurements and the set of photoacoustic measurements. As noted in the embodiments described above, determining the model may comprise selecting the model from a predetermined set of candidate models. In such embodiments, the method may further comprise performing a fitting procedure to select the model from the predetermined set of candidate models having the best fit with data derived from the correlation between the set of reference blood pressure measurements and the set of photoacoustic measurements. As also noted, the fitting procedure may be performed by an ML model, and also may result in the determination of one or more model parameters.

Additionally, according to some embodiments, recalibration may be performed. In such embodiments, the method may further comprise determining to recalibrate the apparatus, and prompting the person to perform a new set of activities. As such, some embodiments may comprise prompting the person to perform the new set of activities, and provide an indication of the recalibration via the UI. The UI may further provide audio and/or visual prompts to perform the new set of activities.

According to some embodiments, the method 1100 may further comprise estimating the blood pressure using the determined model for doing so. That is, some embodiments may further comprise, subsequent to determining the model, obtaining a subsequent photoacoustic measurement, and determining a blood pressure of the person based at least in part on the subsequent photoacoustic measurement and the model.

Means for performing functionality at block 1140 may comprise a photoacoustic sensor system 701, acoustic sensor system 702, motion sensor system 703, control system 706, and/or other components of a PAPG device or similar apparatus, as illustrated in FIG. 7.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

Implementation examples are described in the following numbered clauses:

Clause 1: An apparatus comprising: a control system configured to: obtain activity information indicative of an activity performed by an apparatus user, and update a model for determining blood pressure of the apparatus user based at least in part on the obtained activity information; a light source system including a light-emitting component; and a receiver system configured to detect an acoustic wave corresponding to a photoacoustic response of a blood vessel of the apparatus user to light emitted by the light source system; and wherein the control system is further configured to estimate a blood pressure based at least in part on the updated model and the acoustic wave.

Clause 2: The apparatus of clause 1, wherein, to obtain the activity information, the control system is configured to obtain: an identification of the activity, an indication of a category of the activity, sensor data indicative of the activity, or any combination thereof.

Clause 3: The apparatus of any one of clauses 1-2 further comprising one or more sensors, wherein the control system is configured to obtain the activity information using data from the one or more sensors.

Clause 4: The apparatus of clause 3 wherein the one or more sensors comprise: a gyroscope, an accelerometer, a magnetometer, an altimeter, an inertial measurement unit (IMU), or any combination thereof.

Clause 5: The apparatus of any one of clauses 1-4 wherein, to obtain the activity information, the control system is configured to receive the activity information from a device communicatively coupled with the apparatus.

Clause 6: The apparatus of any one of clauses 1-5 wherein the model includes a plurality of features correlated to blood pressure, and wherein to update the model, the control system is configured to: add one or more features to the plurality of features, subtract one or more features from the plurality of features, adjust one or more weights applied to the plurality of features, or any combination thereof.

Clause 7: The apparatus of clause 6 wherein the plurality of features includes historical activity information, and wherein to update the model, the control system is configured to update the historical activity information based at least in part on the obtained activity information.

Clause 8: The apparatus of any one of clauses 1-7 wherein the control system is configured to a derive a photoacoustic plethysmography (PAPG) measurement from the acoustic wave.

Clause 9: The apparatus of clause 8 wherein, to derive the PAPG measurement, the control system is configured to derive a heart rate waveform (HRW), a pulse transit time (PTT), a pulse wave velocity (PWV), or any combination thereof.

Clause 10: A method of blood pressure estimation, the method comprising: obtaining activity information indicative of an activity performed by a person; updating a model for determining blood pressure of the person based at least in part on the obtained activity information; detecting an acoustic wave corresponding to a photoacoustic response of a blood vessel of the person to light emitted by a light source system; and estimating a blood pressure based at least in part on the updated model and the acoustic wave.

Clause 11: The method of clause 10, further comprising controlling the light source system to emit the light.

Clause 12: The method of clause 11 wherein the light source system is incorporated into an apparatus used by the person, and wherein detecting the acoustic wave is performed by a receiver system of the apparatus.

Clause 13: The method of clause 12 wherein obtaining the activity information comprises receiving the activity information, at the apparatus, from a device communicatively coupled with the apparatus.

Clause 14: The method of any one of clauses 12-13 wherein the apparatus comprises a wearable apparatus worn by the person.

Clause 15: The method of any one of clauses 10-14 wherein the activity information comprises: an identification of the activity, an indication of a category of the activity, sensor data indicative of the activity, or any combination thereof.

Clause 16: The method of any one of clauses 10-15 wherein the activity information is obtained from one or more sensors.

Clause 17: The method of clause 16 wherein the one or more sensors comprise: a gyroscope, an accelerometer, a magnetometer, an altimeter, an inertial measurement unit (IMU), or any combination thereof.

Clause 18: The method of any one of clauses 10-17 wherein the model includes a plurality of features correlated to blood pressure, and wherein updating the model comprises: adding one or more features to the plurality of features, subtracting one or more features from the plurality of features, adjusting one or more weights applied to the plurality of features, or any combination thereof.

Clause 19: The method of clause 18 wherein the plurality of features includes historical activity information, and wherein updating the model comprises updating the historical activity information based at least in part on the obtained activity information.

Clause 20: The method of any one of clauses 10-19 further comprising deriving a photoacoustic plethysmography (PAPG) measurement from the acoustic wave.

Clause 21: The method of clause 20 the PAPG measurement comprises a heart rate waveform (HRW), a pulse transit time (PTT), a pulse wave velocity (PWV), or any combination thereof.

Clause 22: An apparatus comprising: means for obtaining activity information indicative of an activity performed by a person; means for updating a model for determining blood pressure of the person based at least in part on the obtained activity information; means for detecting an acoustic wave corresponding to a photoacoustic response of a blood vessel of the person to light emitted by a light source system; and means for estimating a blood pressure based at least in part on the updated model and the acoustic wave.

Clause 23: The apparatus of clause 22, wherein the apparatus comprises a wearable apparatus configured to detect the acoustic wave and estimate the blood pressure when worn by the person.

Clause 24: The apparatus of any one of clauses 22-23 wherein the means for obtaining the activity information comprises means for obtaining: an identification of the activity, an indication of a category of the activity, sensor data indicative of the activity, or any combination thereof.

Clause 25: The apparatus of any one of clauses 22-24 wherein the means for obtaining the activity information comprise means for obtaining the activity information from one or more sensors.

Clause 26: The apparatus of clause 25 wherein the one or more sensors comprise: a gyroscope, an accelerometer, a magnetometer, an altimeter, an inertial measurement unit (IMU), or any combination thereof.

Clause 27: The apparatus of any one of clauses 22-26 wherein the model includes a plurality of features correlated to blood pressure, and wherein the means for updating the model comprises: means for adding one or more features to the plurality of features, means for subtracting one or more features from the plurality of features, means for adjusting one or more weights applied to the plurality of features, or any combination thereof.

Clause 28: The apparatus of clause 27 wherein the plurality of features includes historical activity information, and wherein the means for updating the model comprises means for updating the historical activity information based at least in part on the obtained activity information.

Clause 29: The apparatus of any one of clauses 22-28 further comprising means for deriving a photoacoustic plethysmography (PAPG) measurement from the acoustic wave.

Clause 30: The apparatus of clause 29 the PAPG measurement comprises a heart rate waveform (HRW), a pulse transit time (PTT), a pulse wave velocity (PWV), or any combination thereof.

Clause 31: An apparatus comprising: a light source system including a light-emitting component; and a receiver system configured to perform photoacoustic measurements by detecting acoustic waves corresponding to photoacoustic responses of a blood vessel of an apparatus user to light emitted by the light source system; a control system configured to: use the light source system and the receiver system to obtain a set of photoacoustic measurements, wherein different photoacoustic measurements of the set of photoacoustic measurements are performed while the apparatus user performs a set of activities; obtain a set of reference blood pressure measurements of the apparatus user, wherein each reference blood pressure measurement of the set of reference blood pressure measurements corresponds to a respective photoacoustic measurement of the set of photoacoustic measurements; and determine a model for estimating blood pressure of the apparatus user from subsequent photoacoustic measurements based on a correlation between the set of reference blood pressure measurements and the set of photoacoustic measurements.

Clause 32: The apparatus of clause 31, wherein the control system is further configured to, subsequent to determining the model: use the light source system and the receiver system to obtain a subsequent photoacoustic measurement; and determine a blood pressure of the apparatus user based at least in part on the subsequent photoacoustic measurement and the model.

Clause 33: The apparatus of any one of clauses 31-32 wherein the control system is configured to obtain the set of reference blood pressure measurements from a data source comprising a device communicatively coupled with the apparatus, one or more sensors of the apparatus, or both.

Clause 34: The apparatus of clause 33, wherein the data source comprises electrocardiogram (EKG) or oscillometry device.

Clause 35: The apparatus of any one of clauses 31-34 wherein, to determine the model, the control system is configured to select the model from a predetermined set of candidate models.

Clause 36: The apparatus of clause 35 wherein, to select the model, the control system is configured to perform a fitting procedure to select the model from the predetermined set of candidate models having the best fit with data derived from the correlation between the set of reference blood pressure measurements and the set of photoacoustic measurements.

Clause 37: The apparatus of any one of clauses 31-36 wherein the control system is further configured to: determine to recalibrate the apparatus; and prompt the apparatus user to perform a new set of activities.

Clause 38: The apparatus of clause 37 wherein the apparatus comprises a user interface (UI) and, to prompt the apparatus user to perform the new set of activities, the control system is configured to provide an indication of the recalibration via the UI.

Clause 39: The apparatus of any one of clauses 31-38 wherein the set of photoacoustic measurements comprise a heart rate waveform (HRW), a pulse transit time (PTT), a pulse wave velocity (PWV), or any combination thereof.

Clause 40: An apparatus having means for performing the functions performed by the apparatuses of any one of clauses 1-9 or 31-39.

Clause 41: A non-transitory computer-readable medium storing instructions, the instructions comprising code for performing the functions performed by the apparatuses of any one of clauses 1-9 or 31-39.

Clause 42: A method for performing the functions performed by the apparatuses of any one of clauses 1-9 or 31-39.

Clause 43: A system comprising one or more devices configured to perform the functions performed by the apparatuses of any one of clauses 1-9 or 31-39.

What is claimed:

1. An apparatus comprising:

a control system configured to:

obtain activity information indicative of an activity performed by an apparatus user, wherein the activity information comprises an identification of the activity, an indication of a category of the activity, or any combination thereof, and adjust a correlation model that correlates a plurality of acoustic-wave-derived features from photoacoustic plethysmography (PAPG) measurements to blood pressure values for the apparatus user, based at least in part on the obtained activity information, wherein to adjust the correlation model, the control system is configured to:

add one or more features to the plurality of acoustic-wave-derived features, subtract one or more features from the plurality of acoustic-wave-derived features, adjust one or more weights applied to the plurality of acoustic-wave-derived features, or any combination thereof;

a light source system including a light-emitting component; and a receiver system configured to detect an acoustic wave corresponding to a photoacoustic response of a blood vessel of the apparatus user to light emitted by the light source system; and wherein the control system is further configured to estimate a blood pressure based at least in part on the adjusted correlation model and the acoustic wave.

2. The apparatus of claim 1, wherein, to obtain the activity information, the control system is configured to obtain sensor data indicative of the activity.

3. The apparatus of claim 1, further comprising one or more sensors, wherein the control system is configured to obtain the activity information using data from the one or more sensors.

4. The apparatus of claim 3, wherein the one or more sensors comprise:

a gyroscope, an accelerometer, a magnetometer, an altimeter, an inertial measurement unit (IMU), or any combination thereof.

5. The apparatus of claim 1, wherein, to obtain the activity information, the control system is configured to receive the activity information from a device communicatively coupled with the apparatus.

6. The apparatus of claim 1, wherein the plurality of acoustic-wave-derived features includes historical activity information, and wherein to adjust the correlation model, the control system is configured to update the historical activity information based at least in part on the obtained activity information.

7. The apparatus of claim 1, wherein, to derive the PAPG measurement, the control system is configured to derive a heart rate waveform (HRW), a pulse transit time (PTT), a pulse wave velocity (PWV), or any combination thereof.

8. A method of blood pressure estimation, the method comprising:

obtaining activity information indicative of an activity performed by a person, wherein the activity information comprises an identification of the activity, an indication of a category of the activity, or any combination thereof;

adjusting a correlation model that correlates a plurality of acoustic-wave-derived features from photoacoustic plethysmography (PAPG) measurements to blood pressure values for the person, based at least in part on the obtained activity information, wherein adjusting the correlation model comprises:

adding one or more features to the plurality of acoustic-wave-derived features, subtracting one or more features from the plurality of acoustic-wave-derived features, adjusting one or more weights applied to the plurality of acoustic-wave-derived features, or any combination thereof;

detecting an acoustic wave corresponding to a photoacoustic response of a blood vessel of the person to light emitted by a light source system; and estimating a blood pressure based at least in part on the adjusted correlation model and the acoustic wave.

9. The method of claim 8, further comprising controlling the light source system to emit the light.

10. The method of claim 9, wherein the light source system is incorporated into an apparatus used by the person, and wherein detecting the acoustic wave is performed by a receiver system of the apparatus.

11. The method of claim 10, wherein obtaining the activity information comprises receiving the activity information, at the apparatus, from a device communicatively coupled with the apparatus.

12. The method of claim 10, further comprising performing the method while the apparatus is worn by the person.

13. The method of claim 8, wherein obtaining the activity information comprises obtaining sensor data indicative of the activity.

14. The method of claim 8, wherein the activity information is obtained from one or more sensors.

15. The method of claim 14, further comprising obtaining the activity information using one or more sensors comprising:

a gyroscope, an accelerometer, a magnetometer, an altimeter, an inertial measurement unit (IMU), or any combination thereof.

16. The method of claim 8, wherein the plurality of acoustic-wave-derived features includes historical activity information, and wherein adjusting the correlation model comprises adjusting the historical activity information based at least in part on the obtained activity information.

17. The method of claim 8, the PAPG measurement comprises a heart rate waveform (HRW), a pulse transit time (PTT), a pulse wave velocity (PWV), or any combination thereof.

18. An apparatus comprising:

means for obtaining activity information indicative of an activity performed by a person, wherein the activity information comprises an identification of the activity, an indication of a category of the activity, or any combination thereof;

means for adjusting a correlation model that correlates a plurality of acoustic-wave-derived features from photoacoustic plethysmography (PAPG) measurements to blood pressure values for the person based at least in part on the obtained activity information, wherein the means for adjusting the correlation model comprise means for:

adding one or more features to the plurality of acoustic-wave-derived features, subtracting one or more features from the plurality of acoustic-wave-derived features, adjusting one or more weights applied to the plurality of acoustic-wave-derived features, or any combination thereof;

means for detecting an acoustic wave corresponding to a photoacoustic response of a blood vessel of the person to light emitted by a light source system; and means for estimating a blood pressure based at least in part on the adjusted correlation model and the acoustic wave.

19. The apparatus of claim 18, wherein the apparatus comprises a wearable apparatus configured to detect the acoustic wave and estimate the blood pressure when worn by the person.

20. The apparatus of claim 18, wherein the means for obtaining the activity information comprises means for obtaining sensor data indicative of the activity.

21. The apparatus of claim 18, wherein the means for obtaining the activity information comprise means for obtaining the activity information from one or more sensors.

22. The apparatus of claim 21, wherein the one or more sensors comprise:

a gyroscope, an accelerometer, a magnetometer, an altimeter, an inertial measurement unit (IMU), or any combination thereof.

23. The apparatus of claim 18, wherein the plurality of acoustic-wave-derived features includes historical activity information, and wherein the means for adjusting the correlation model comprises means for adjusting the historical activity information based at least in part on the obtained activity information.

24. The apparatus of claim 18, the PAPG measurement comprises a heart rate waveform (HRW), a pulse transit time (PTT), a pulse wave velocity (PWV), or any combination thereof.

* * * * *